(12) United States Patent
Fanton et al.

(10) Patent No.: US 12,303,256 B2
(45) Date of Patent: May 20, 2025

(54) SYSTEMS, DEVICES, AND METHODS FOR ASSESSMENT OF BRAIN INJURY

(71) Applicant: The Board of Trustees of the Leland Stanford Junior University, Stanford, CA (US)

(72) Inventors: Michael G. Fanton, Stanford, CA (US); David B. Camarillo, Aptos, CA (US); Kaveh Laksari, Stanford, CA (US); Lyndia Chun Wu, Stanford, CA (US); Mehmet Kurt, Stanford, CA (US); Taylor H. Nguyen, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 802 days.

(21) Appl. No.: 17/413,918

(22) PCT Filed: Dec. 12, 2019

(86) PCT No.: PCT/US2019/066088
§ 371 (c)(1),
(2) Date: Jun. 14, 2021

(87) PCT Pub. No.: WO2020/123875
PCT Pub. Date: Jun. 18, 2020

(65) Prior Publication Data
US 2022/0061702 A1    Mar. 3, 2022

Related U.S. Application Data

(60) Provisional application No. 62/778,879, filed on Dec. 12, 2018.

(51) Int. Cl.
*A61B 5/11* (2006.01)
*A61B 5/00* (2006.01)
*G16H 50/50* (2018.01)

(52) U.S. Cl.
CPC .......... *A61B 5/1122* (2013.01); *A61B 5/0002* (2013.01); *A61B 5/6803* (2013.01);
(Continued)

(58) Field of Classification Search
CPC ... A61B 5/1122; A61B 5/0002; A61B 5/6803; A61B 5/7267; A61B 2503/10; A61B 2562/0219; G16H 50/50
(Continued)

(56) References Cited

U.S. PATENT DOCUMENTS 8,761,437 B2    6/2014  Kirovski et al.
9,129,499 B2    9/2015  Howard et al.
(Continued)

FOREIGN PATENT DOCUMENTS

WO    2020123875 A1    6/2020

OTHER PUBLICATIONS

International Preliminary Report on Patentability for International Application No. PCT/US2019/066088, Report issued Jun. 8, 2021, Mailed on Jun. 24, 2021, 15 Pgs.
(Continued)

*Primary Examiner* — Christine H Matthews
*Assistant Examiner* — Chanel J Jhin
(74) *Attorney, Agent, or Firm* — KPPB LLP

(57) ABSTRACT

Systems, methods and devices for detecting a concussive event are provided. A computational classifier may be trained and utilized for detecting a concussive event in real-time. Head kinematics can be measured and a head
(Continued)

kinematic metric determined, which can be utilized within the classifier to detect a concussive event.

**20 Claims, 16 Drawing Sheets
(13 of 16 Drawing Sheet(s) Filed in Color)**

(52) U.S. Cl.
CPC ........... *A61B 5/7267* (2013.01); *G16H 50/50* (2018.01); *A61B 2503/10* (2013.01); *A61B 2562/0219* (2013.01)

(58) Field of Classification Search
USPC ........................................................ 600/595
See application file for complete search history.

(56) References Cited

U.S. PATENT DOCUMENTS

| | | |
|---|---|---|
| 9,289,176 B2 | 3/2016 | Benzel et al. |
| 9,308,642 B2 | 4/2016 | Sugar et al. |
| 2009/0158509 A1 | 6/2009 | Ghajar |
| 2012/0041330 A1 | 2/2012 | Prichep et al. |
| 2012/0220893 A1 | 8/2012 | Benzel et al. |
| 2013/0217977 A9 | 8/2013 | Cooner |
| 2016/0321425 A1 | 11/2016 | Ji et al. |
| 2017/0156635 A1 | 6/2017 | Kuo et al. |
| 2017/0238850 A1 | 8/2017 | Gonzales et al. |

OTHER PUBLICATIONS

International Search Report and Written Opinion for International Application No. PCT/US2019/066088, search completed on Feb. 5, 2020, Mailed on Feb. 25, 2020, 23 Pgs.
"Standard Performance Specification for Newly Manufactured Football Helmets", National Operating Committee on Standards for Athletic Equipment, NOCSAE Doc: (ND)002-11m12, May 2012, 8 pgs.
Baugh et al., "Chronic traumatic encephalopathy: neurodegeneration following repetitive concussive and subconcussive brain trauma", Brain Imaging and Behavior, vol. 6, Issue 2, Jun. 2012, pp. 244-254.
Bland et al., "STAR Methodology for Bicycle Helmets", Virginia Polytechnic Institute and State University, Virginia Tech Helmet Lab, May 30, 2018, 6 pgs.
Broglio et al., "National Athletic Trainers' Association Position Statement: Management of Sport Concussion", Journal of Athletic Training, vol. 49, No. 2, Mar./Apr. 2014, pp. 245-265.
De Long et al., "Comparing the areas under two or more correlated receiver operating characteristic curves: a nonparametric approach", Biometrics, Sep. 1998, vol. 44, No. 3, pp. 837-845.
Dekosky et al., "Acute and chronic traumatic encephalopathies: pathogenesis and biomarkers", Nature Reviews Neurology, vol. 9, Apr. 5, 2013, pp. 192-200.
Echemendia et al., "The Sport Concussion Assessment Tool 5th Edition (SCAT5)", British Journal of Sports Medicine, vol. 51, Feb. 14, 2017, pp. 851-858.
Elliott et al., "Accounting for sampling variability, injury underreporting, and sensor error in concussion injury risk curves", Journal of Biomechanics, vol. 48, No. 12, Sep. 18, 2015, pp. 3059-3065.
Ewing et al., "The Effect of Duration, Rate of Onset, and Peak Sled Acceleration on the Dynamic Response of the Human Head and Neck", SAE Technical Paper 760800, Feb. 1, 1976, 40 pgs.
Fanton et al., "Dependency of Head Impact Rotation on Head-Neck Positioning and Soft Tissue Forces", IEEE Transactions on Biomedical Engineering, vol. 66, No. 4, Aug. 20, 2018, pp. 988-999.
Gabler et al., "Assessment of Kinematic Brain Injury Metrics for Predicting Strain Responses in Diverse Automotive Impact Conditions", Annals of Biomedical Engineering, vol. 44, No. 12, Dec. 2016, pp. 3705-3718.
Gabler et al., "Development of a Second-Order System for Rapid Estimation of Maximum Brain Strain", Annals of Biomedical Engineering, vol. 47, No. 9, Dec. 2018, pp. 1971-1981.
Gabler et al., "Development of a Single-Degree-of-Freedom Mechanical Model for Predicting Strain-Based Brain Injury Responses", Journal of Biomechanical Engineering, vol. 140, No. 3, Jan. 17, 2018, 13 pgs.
Gadd, "Use of a Weighted-Impulse Criterion for Estimating Injury Hazard", Proceedings of the 10th Stapp Car Crash Conference, SAE Technical Paper 660793, Feb. 1, 1966, 6 pgs.
Gennarelli, "Future Directions in Brain Injury Research", Progress in Neurological Surgery, vol. 28, 2014, pp. 243-250.
Gennarelli et al., "Directional Dependence of Axonal Brain Injury due to Centroidal and Non-Centroidal Acceleration", SAE Technical Paper 872197, Nov. 1, 1987, 5 pgs.
Giordano et al., "Evaluation of Axonal Strain as a Predictor for Mild Traumatic Brain Injuries Using Finite Element Modeling", SAE Technical Paper 2014-22-0002, Nov. 10, 2014, 33 pgs.
Giordano et al., "The influence of anisotropy on brain injury prediction", Journal of Biomechanics, vol. 47, No. 5, Mar. 21, 2014, pp. 1052-1059.
Henn et al., "Crash Tests and the Head Injury Criterion", Teaching Mathematics and its Applications: An International Journal of the IMA, vol. 17, No. 4, Dec. 1, 1998, pp. 162-170.
Hernandez et al., "Six Degree-of-Freedom Measurements of Human Mild Traumatic Brain Injury", Annals of Biomedical Engineering, vol. 43, No. 8, Aug. 2015, pp. 1918-1934.
Hernandez et al., "Voluntary Head Rotational Velocity and Implications for Brain Injury Risk Metrics", Journal of Neurotrauma, vol. 36, No. 7, Oct. 22, 2018, pp. 1125-1135.
Kimpara et al., "Mild Traumatic Brain Injury Predictors Based on Angular Accelerations During Impacts", Annals of Biomedical Engineering, vol. 40, No. 1, Jan. 2012, pp. 114-126.
King et al., "Logistic Regression in Rare Events Data", Society for Political Methodology, Political Analysis, vol. 9, Feb. 16, 2001, pp. 137-163.
Kleiven, "Predictors for Traumatic Brain Injuries Evaluated through Accident Reconstructions", Stapp Car Crash Journal, vol. 51, Oct. 2007, 35 pgs.
Kleiven et al., "Correlation of an FE Model of the Human Head with Local Brain Motion—Consequences for Injury Prediction", Stapp Car Crash Journal, vol. 46, Nov. 2002, pp. 123-144.
Kornhauser, "Theoretical Prediction of the Effect of Rate-of-onset on Man's G-tolerance", Aerospace Medicine, vol. 32, May 1961, pp. 412-421.
Kuo et al., "Pilot Findings of Brain Displacements and Deformations during Roller Coaster Rides", Journal of Neurotrauma, vol. 34, No. 22, Nov. 15, 2017, pp. 3198-3205.
Kurt et al., "Modeling and Optimization of Airbag Helmets for Preventing Head Injuries in Bicycling", Annals of Biomedical Engineering, vol. 45, No. 4, Apr. 2017, pp. 1148-1160.
Laksari et al., "Computational simulation of the mechanical response of brain tissue under blast loading", Biomechanics and Modeling in Mechanobiology, vol. 14, No. 3, Jun. 2015, pp. 459-472.
Laksari et al., "Constitutive model for brain tissue under finite compression", Journal of Biomechanics, vol. 45, No. 4, Feb. 23, 2012, pp. 642-646.
Laksari et al., "Mechanistic Insights into Human Brain Impact Dynamics through Modal Analysis", Physical Review Letters, vol. 120, No. 13, Mar. 30, 2018, 138101, 7 pgs.
Laksari et al., "Multi-directional dynamic model for traumatic brain injury detection", https://arxiv.org/abs/1812.07731, Dec. 19, 2018, 42 pgs.
Laksari et al., "Resonance of human brain under head acceleration", Journal of the Royal Society Interface, vol. 12, No. 108, Jul. 6, 2015, 9 pgs.
Low et al., "A Lumped Parameter Approach to Simulate the Rotational Head Motion", International Research Council on Biokinetics of Impacts (IRCOBI), 1987, pp. 203-215.
Margulies et al., "A proposed tolerance criterion for diffuse axonal injury in man", Journal of Biomechanics, vol. 25, No. 8, Aug. 1992, pp. 917-923.

(56) References Cited

OTHER PUBLICATIONS

Mckee et al., "Chronic Traumatic Encephalopathy in Athletes: Progressive Tauopathy After Repetitive Head Injury", Journal of Neuropathology and Experimental Neurology, vol. 68, No. 7, Jul. 2009, pp. 709-735.
Newman, "A Generalized Acceleration Model for Brain Injury Threshold (GAMBIT)", Proceedings of International Research Council on Biokinetics of Impacts, 1986, pp. 121-131.
Newman et al., "A Proposed New Biomechanical Head Injury Assessment Function—The Maximum Power Index", Stapp Car Crash Journal, vol. 44, Nov. 2000, pp. 215-247.
Ommaya et al., "Cerebral Concussion and Traumatic Unconsciousness: Correlation of Experimental and Clinical Observations of Blunt Head Injuries", Brain, vol. 97, No. 1, Jan. 1, 1974, pp. 633-654.
Ommaya et al., "Tolerances for cerebral concussion from head impact and whiplash in primates", Journal of Biomechanics, vol. 4, No. 1, Jan. 1971, pp. 13-21.
Pellman et al., "Concussion in Professional Football: Reconstruction of Game Impacts and Injuries", Neurosurgery, vol. 53, No. 4, Sep. 2003, pp. 799-814.
Raghupathi et al., "Traumatic Axonal Injury after Closed Head Injury in the Neonatal Pig", Journal of Neurotrauma, vol. 19, No. 7, 2002, pp. 843-853.
Rowson et al., "Brain Injury Prediction: Assessing the Combined Probability of Concussion Using Linear and Rotational Head Acceleration", Annals of Biomedical Engineering, vol. 41, No. 5, May 2013, pp. 873-882.
Rowson et al., "Hockey STAR: A Methodology for Assessing the Biomechanical Performance of Hockey Helmets", Annals of Biomedical Engineering, vol. 43, No. 10, Oct. 2015, pp. 2429-2443.
Rowson et al., "Linear and Angular Head Acceleration Measurements in Collegiate Football", Journal of Biomechanical Engineering, vol. 131, No. 6, Jun. 2009, 7 pgs.
Rowson et al., "Rotational Head Kinematics in Football Impacts: An Injury Risk Function for Concussion", Annals of Biomedical Engineering, vol. 40, No. 1, Jan. 2012, pp. 1-13.
Sahoo et al., "Brain injury tolerance limit based on computation of axonal strain", Accident Analysis & Prevention, vol. 92, Jul. 2016, pp. 53-70.
Sanchez et al., "A reanalysis of football impact reconstructions for head kinematics and finite element modeling", Clinical Biomechanics, vol. 64, Mar. 14, 2018, pp. 82-89.
Stalnaker et al., "Driving Point Impedance Characteristics of the Head", Journal of Biomechanics, vol. 4, No. 2, Mar. 1971, pp. 127-130, IN1, IN3, 131-139.
Sullivan et al., "White matter tract-oriented deformation predicts traumatic axonal brain injury and reveals rotational direction-specific vulnerabilities", Biomechanics and Modeling in Mechanobiology, vol. 14, No. 4, Aug. 2015, pp. 877-896.
Sye et al., "High school rugby players' understanding of concussion and return to play guidelines", British Journal of Sports Medicine, vol. 40, No. 12, Dec. 2006, pp. 1003-1005.
Takhounts et al., "Development of Brain Injury Criteria (BrIC)", Stapp Car Crash Journal, vol. 57, Nov. 2013, pp. 243-266.
Takhounts et al., "Investigation of Traumatic Brain Injuries Using the Next Generation of Simulated Injury Monitor (SIMon) Finite Element Head Model", Stapp Car Crash Journal, vol. 52, Nov. 2008, 32 pgs.
Tyson et al., "Adult Football STAR Methodology", Virginia Polytechnic Institute and State University, Virginia Tech Helmet Lab, Mar. 30, 2018, 4 pgs.
Williamson et al., "Converging evidence for the under-reporting of concussions in youth ice hockey", British Journal of Sports Medicine, vol. 40, No. 2, Jan. 23, 2006, pp. 128-132.
Wu et al., "Bandwidth and sample rate requirements for wearable head impact sensors", Journal of Biomechanics, vol. 49, No. 13, Sep. 6, 2016, pp. 2918-2924.
Wu et al., "Detection of American Football Head Impacts Using Biomechanical Features and Support Vector Machine Classification", Scientific Reports, vol. 8, No. 855, Dec. 21, 2017, 14 pgs.
Zou et al., "Separating brain motion into rigid body displacement and deformation under low-severity impacts", Journal of Biomechanics, vol. 40, No. 6, 2007, pp. 1183-1191.
Zou et al., "The Effect of Brain Mass and Moment of Inertia on Relative Brain-Skull Displacement During Low-Severity Impacts", International Journal of Crashworthiness, vol. 12, No. 4, Oct. 2007, pp. 341-353.

B. Inclusion of brain anisotropy

SYSTEMS, DEVICES, AND METHODS FOR ASSESSMENT OF BRAIN INJURY

CROSS REFERENCE TO RELATED APPLICATIONS

This application is a national stage of PCT Patent Application No. PCT/US2019/066088, entitled "Systems, Devices, and Methods for Assessment of Brain Injury" to Michael G. Fanton et al., filed Dec. 12, 2019, which claims priority to U.S. Provisional Application Ser. No. 62/778,879, entitled "Multi-directional dynamic model for TBI detection" to David B. Camarillo et al., filed Dec. 12, 2018, the disclosure of which is incorporated herein by reference in its entirety.

FIELD OF THE INVENTION

The present invention relates to assessment of brain injury and more specifically to systems, devices, and methods to detect a concussive event.

BACKGROUND OF THE INVENTION

Mild traumatic brain injury (mTBI), or concussion, has received heightened awareness due to its adverse effects on not only professional athletes and military personnel, but more broadly the general public. Aside from acute neurocognitive deficits, mounting evidence suggests increased risk of chronic neurodegeneration with repeated mTBI. There have been multiple reports of contact athletes and service veterans suffering from memory loss, behavioral changes, and motor function abnormalities later in life. In severe cases, retired professional football players in their middle ages have shown extreme changes in personality and suicidal tendencies. Return to play guidelines and legislations have been introduced to protect athletes from repeat trauma and to reduce the risk of long-term brain damage. Despite increased awareness of mTBI, timely diagnosis and prevention of this injury is difficult due to a lack of understanding of injury mechanisms.

SUMMARY OF THE INVENTION

Many embodiments are directed to systems, devices, and methods to detect a concussive event. Several embodiments utilize a head-mounted device measure head motion and a computational classifier to determine whether an impact resulted in a concussive event.

In an embodiment of a system for assessment of head impacts, the system includes a head-mounted device capable of being worn on or secured to the head of an individual. The device is further capable of measuring angular head motion when worn or secured to the head of an individual. The system includes memory in communication with the device via an interface. The system includes a processor that reads instructions stored in the memory. The instructions direct the processor to obtain head kinematic measurements in at least one anatomical direction from the head-mounted device. The instructions direct the processor to compute, utilizing the head kinematic measurements, a head kinematic metric for the at least one anatomical direction. The instructions direct the processor to determine that a concussive event occurs utilizing a trained classifier and the head kinematic metric.

In another embodiment, the head mounted device is a helmet, a mouth guard, a hat, an ear protection, an eye-wear, a skin-mounted sensor, or a head band.

In yet another embodiment, the system further includes a gyroscope, a rotational accelerometer, or an array of linear accelerometers to measure head angular motion.

In a further embodiment, the head kinematic metric is peak angular acceleration ($\vec{\alpha}$), peak change in rotational velocity ($\Delta \vec{\omega}$), or peak translational acceleration ($\vec{a}$).

In still yet another embodiment, the head kinematic metric is a brain angle metric that is computed utilizing a mass-deformation brain model.

In yet a further embodiment, the mass-deformation brain model is a mass-spring-damper model.

In an even further embodiment, the mass-spring-damper model models the rotational deformation of the brain from skull loading.

In yet an even further embodiment, the mass-spring-damper model computes motion for each anatomical direction utilizing the following equation:

$$I(\ddot{\theta}_{brain} + \ddot{\theta}_{skull}) = -k\theta_{brain} - c\dot{\theta}_{brain}$$

wherein I is the moment of inertia of the mass, k and c are the stiffness and damping values of the system, and $\theta_{brain}$ and $\theta_{skull}$ represent the angles of the brain (the mass) and the skull (the base).

In still yet an even further embodiment, the head kinematic measurements include head angle motion measurements in at least three anatomical directions.

In still yet an even further embodiment, the three anatomical directions are coronal, axial, and sagittal.

In still yet an even further embodiment, the classifier is a regression model.

In still yet an even further embodiment, the regression model is a linear regression model, a logistic regression model, an elastic net regression model, a polynomial regression model, a stepwise regression model, a ridge regression model, a LASSO regression model, or a combined regression model.

In still yet an even further embodiment, the regression model is the following logistic model:

$$p_{injury} = (1 + e^{-\beta_0 - \Sigma \beta_i x_i})^{-1}$$

where $p_{injury}$ is the probability of concussive event, $x_i$ are the components of the injury criterion, and $\beta_i$ are the fitted coefficients, with i=1, ..., n, representing each of the at least one anatomical directions and n representing the number of anatomical directions.

In still yet an even further embodiment, the concussive event is determined by a risk curve that determines the percent likelihood that a head impact was a concussive event.

In still yet an even further embodiment, a threshold is utilized to signify whether the head impact was concussive event.

In still yet an even further embodiment, the threshold is set to capture at least 50%, 60%, 70%, 80%, 90%, 95%, or 99% A of concussive events.

In still yet an even further embodiment, the determination that a concussive event occurs is determined in real time.

In still yet an even further embodiment, the instructions further direct the processor to signal in real time that the concussive event has occurred.

In still yet an even further embodiment, the memory and processor are incorporated within the head-mounted device.

In still yet an even further embodiment, the memory and processor are remote from the head-mounted device.

In still yet an even further embodiment of a method for assessment of head impacts, the method measures head kinematics in at least one anatomical direction of an individual via a head-mounted device that is worn on or secured to the head of the individual. The method communicates between the head-mounted device and a computer the system the head kinematic measurements. The method computes via the computer system a head kinematic metric for the at least one anatomical direction utilizing the head kinematic measurements. The method determines via the computer system that a concussive event occurs utilizing a trained classifier and the brain angle metric.

In still yet an even further embodiment, a gyroscope, a rotational accelerometer, or an array of linear accelerometers is associated with the head-mounted device to measure head angular motion.

In still yet an even further embodiment, the method signals in real time via the computer system that the concussive event has occurred.

In still yet an even further embodiment, the computing system is incorporated within the head-mounted device.

In still yet an even further embodiment, the computing system is remote from the head-mounted device.

In still yet an even further embodiment of a non-transitory machine readable medium containing processor instructions, where execution of the instructions by a processor causes the processor to perform a process, the process retrieves head kinematic measurements from a head-mounted device, wherein the head-mounted device measures head angular motion in at least one anatomical direction of an individual when the head-mounted device is worn on or secured to the head of the individual. The process computes, utilizing the head kinematic measurements, a head kinematic metric for the at least one anatomical direction utilizing the head angular motion measurements. The process determines that a concussive event occurs utilizing a trained classifier and the head kinematic metric.

In still yet an even further embodiment, the process signals in real time via an output interface that the concussive event has occurred.

In still yet an even further embodiment, the processor is incorporated within the head-mounted device.

In still yet an even further embodiment, the processor is remote from the head-mounted device.

In still yet an even further embodiment of a method to perform a medical intervention on an individual based upon the determination that the individual has suffered a concussive event, the method computes or has computed a head kinematic metric for the at least one anatomical direction. The head kinematic metric is computed using head kinematic measurements that are measured via a head-mounted device that is worn on or secured to the head of an individual. The method determines or has determined that the individual has suffered a concussive event utilizing a trained classifier and the head kinematic metric. The method performs a medical intervention on the individual based upon the determination that the individual suffered a concussive event.

In still yet an even further embodiment, the medical intervention is a medical procedure selected from the group consisting of: field test, neurological assessment, cognitive testing, medical imaging and observation.

In still yet an even further embodiment, the medical intervention is administration of a treatment selected from the group consisting of: physical rest, mental rest, and pain and anti-inflammatory medicine.

In still yet an even further embodiment, the individual is an athlete, fighter, military personnel, or epileptic.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features and advantages of the present invention will be better understood by reference to the following detailed description when considered in conjunction with the accompanying data and figures, wherein.

DETAILED DESCRIPTION OF THE DISCLOSURE

Figure 1:
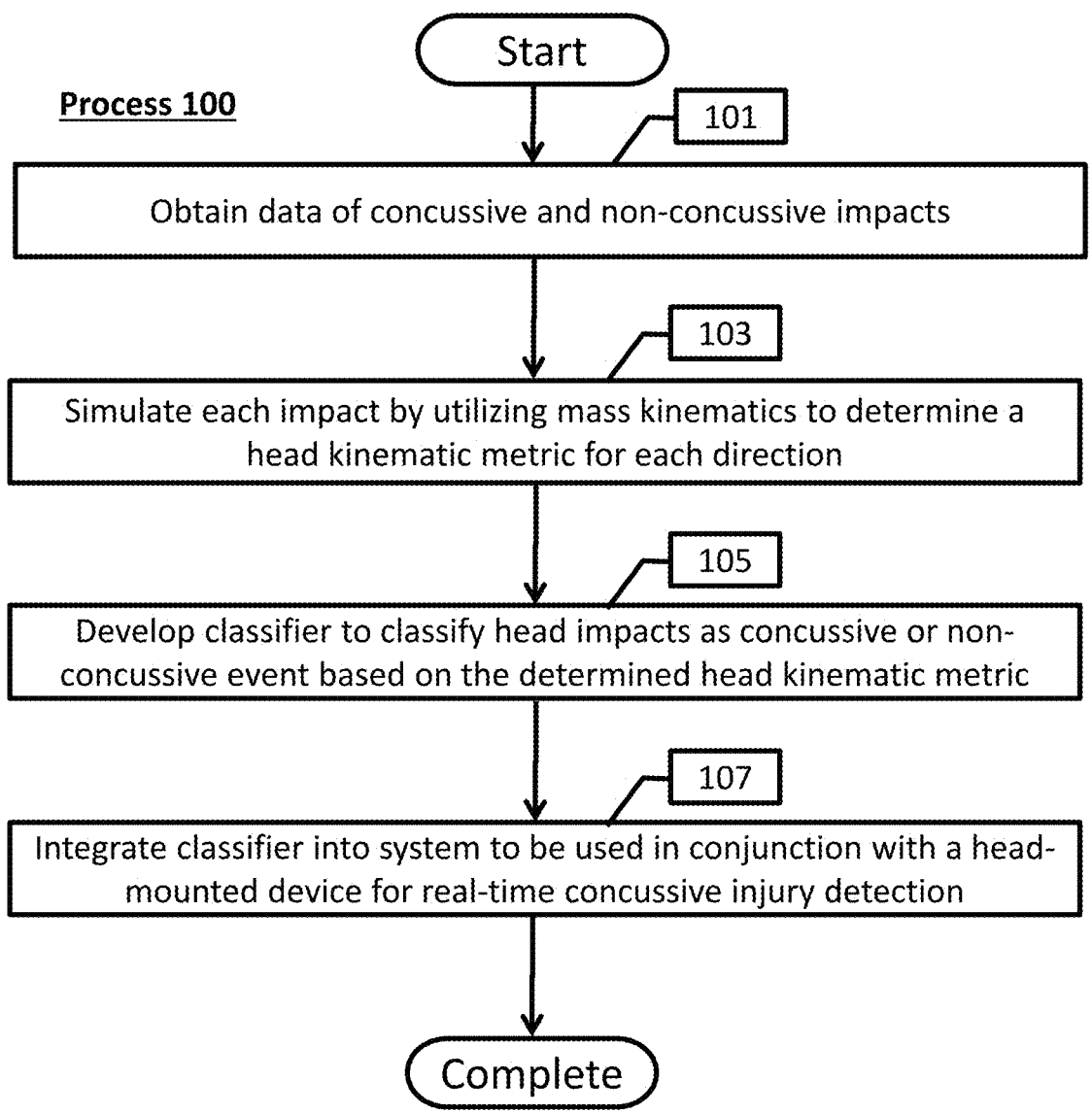
FIG. 1 provides a flow chart for developing a classifier to classify head impacts in accordance with an embodiment.

The embodiments of the invention described herein are not intended to be exhaustive or to limit the invention to precise forms disclosed. Rather, the embodiments selected for description have been chosen to enable one skilled in the art to practice the invention.

Turning now to the drawings, systems, methods, and devices for assessing brain injury status based on real-time determination of head angle motion at an impact are provided. In many embodiments, systems, methods, and/or devices determine whether a concussive event (i.e., mild traumatic brain injury (mTBI) or concussion) has occurred in an individual. In several embodiments, a head-mounted device is utilized to measure head motion and a computational classifier is utilized to determine whether that motion resulted in a concussive event. It is to be understood that a head-mounted device is a device capable of being worn on or secured to the head of an individual.

In a number of embodiments, head motion (i.e., head mass kinematics) is measured in at least one degree freedom. In many of these embodiments, three degrees of freedom are utilized and mass kinematics are measured in three anatomical directions (e.g., coronal, axial, and sagittal). In several embodiments, mass kinematics is utilized to compute a head kinematic metric. Any appropriate head kinematic metric can be utilized, including (but not limited to) peak angular acceleration ($\vec{\alpha}$), peak change in rotational velocity ($\Delta \vec{\omega}$), peak translational acceleration ($\vec{a}$), and a brain angle metric.

Several embodiments are also directed to utilization of a mass-deformation brain model to determine a brain angle metric (e.g., maximum brain angle). In many embodiments, a mass-deformation brain model is a mass-spring-damper model that measures mass kinematics in at least one degree of freedom.

Many embodiments are directed to head-mounted systems and/or devices for determining brain angle motion at impact. In several embodiments, head-mounted systems and/or devices further are in communication with a classifier to determine whether an impact is a concussive event as determined by brain angle motion. Various embodiments of head-mounted systems and/or devices incorporate components for measuring head motion and/or acceleration. In some embodiments, a gyroscope, rotational accelerometer, an array of linear accelerometers, or a combination thereof is utilized for measuring head motion and/or acceleration. Head-mounted devices include (but not limited to) helmet, mouthguard, hat, ear protection, eye-wear, skin-mounted sensor, and head band.

Concussive Event Classifier Development

Numerous embodiments are directed to building a computational classifier capable of predicting whether a concussive event occurred utilizing mass kinematics measured at impact. In several embodiments, a concussive event classifier incorporates the measured mass kinematic data. In several embodiments, a concussive event classifier incorporates a mass-deformation brain model that measures brain angle motion in multiple degrees of freedom. In several embodiments, the mass-deformation brain model is a three degree-of-freedom, mass-spring damper model that models the rotational deformation of the brain from skull loading in the three anatomical directions (e.g., coronal, axial, and sagittal). In a number of embodiments, the mass-deformation brain model determines a brain angle metric. In many embodiments, the brain angle metric is a vector of the three peak brain angle values in each direction.

In several embodiments, a head kinematic metric is utilized in a computational classifier to predict whether a concussive event occurred at impact. In some embodiments, the classifier is a regression model. Any appropriate regression model can be utilized, including (but not limited to) linear regression, logistic regression, elastic net regression, polynomial regression, stepwise regression, ridge regression, LASSO regression, and any combined regression models. Accordingly, in many embodiments, a regression model is utilized to distinguish whether an impact was a concussive event (i.e., mTBI or concussion) or a non-concussive event. In numerous embodiments, data sets that include both concussive events and non-concussive events in which the kinematics were measured during the event are utilized to train the model. In some situations, kinematics can be measured by a gyroscope, rotational accelerometer, and/or an array of linear accelerometers with a head-mounted device.

Provided in FIG. 1 is an embodiment of a method to build a concussive event classifier, which may be integrated into a system or device for real-time detection of concussive injury. As shown in FIG. 1, process 100 begins by obtaining (101) data of concussive and non-concussive impacts. The data should include kinematic measurements in at least one degree of freedom. In some embodiments, data includes kinematic measurements in at least three degrees of freedom. Data can be derived from any appropriate head impact events, such as those experienced in a sporting event, combative event, or other events in which concussive events could happen. Sporting events can include (but not limited to) football, wrestling, boxing, mixed martial arts, rugby, hockey, lacrosse, and baseball. Combative events can include (but not limited to) military combat.

Any appropriate device capable of measuring head motion can be utilized to capture data. In many embodiments, a gyroscope, rotational accelerometer, and/or an array of linear accelerometers in association with a head-mounted device is utilized to measure head kinematics. A head-mounted device can include (but not limited to) helmet, mouthguard, hat, ear protection, eye-wear, skin-mounted sensor, and head band.

Any appropriate kinematic measurements can be captured to compute a head kinematic. In several embodiments, kinetic measurements are utilized to determine the maximum brain angle in each anatomical direction. In many embodiments, kinematics are measured in three anatomical directions (e.g., coronal, axial, and sagittal).

As shown in FIG. 1, process 100 optionally simulates (103) each impact from the data set by utilizing the mass kinematic measurements of each impact for each anatomical direction to determine a head kinematic metric for each direction. Any appropriate head kinematic metric can be utilized, including (but not limited to) peak angular acceleration ($\vec{\alpha}$), peak change in rotational velocity ($\Delta \vec{\omega}$), peak translational acceleration ($\vec{a}$), and a brain angle metric.

In embodiments, peak angular acceleration ($\vec{\alpha}$) is a vector defined as the maximum value of the rotational acceleration time series in each anatomical direction:

$$\vec{\alpha} = [\max|\alpha_x|, \max|\alpha_y|, \max|\alpha_z|].$$

Although three anatomical directions are shown (x, y, and z), it is to be understood that any appropriate number of anatomical directions can be utilized, and that at least one anatomical direction is utilized. In some embodiments, the maximum value is retrieved from the entire recorded time series for a given time series.

In embodiments, peak change in rotational velocity ($\Delta\vec{\omega}$) is defined as the largest change in rotational velocity magnitude in each anatomical direction:

$$\Delta\vec{\omega} = |\max \omega_x(t) - \min \omega_x(t), \max \omega_y(t) - \min \omega_y(t), \max \omega_z(t) - \min \omega_z(t)|.$$

Although three anatomical directions are shown (x, y, and z), it is to be understood that any appropriate number of anatomical directions can be utilized, and that at least one anatomical direction is utilized. In some embodiments, the maximum and minimum values for each component are retrieved from the entire recorded time series for a given series.

In embodiments, peak translational acceleration ($\vec{a}$) is defined as the peak absolute value of the translational acceleration vector time series in each anatomical direction:

$$\vec{a} = [a_x, a_y, a_z] = |\vec{a}(t)|.$$

Although three anatomical directions are shown (x, y, and z), it is to be understood that any appropriate number of anatomical directions can be utilized, and that at least one anatomical direction is utilized. In some embodiments, the maximum value is retrieved from the entire recorded time series for a given series.

In a number of embodiments, a mass-deformation brain model is utilized to compute a brain angle metric. Any appropriate mass-deformation brain model may be utilized, such as (for example) a mass-spring-damper model. In many embodiments, the mass-spring-damper brain model is a 3 degrees-of-freedom mechanical analog of the brain. In several embodiments, the brain model is developed assuming the brain has rigid-body motion behavior in each anatomical direction. Accordingly, in these embodiments, a separate mass-spring-damper system is used for each anatomical direction. In many embodiments, the mechanical mass-spring-damper system models the rotational deformation of the brain from skull loading. In some embodiments, the motion for each anatomical direction is computed as follows:

$$I(\ddot{\theta}_{brain} + \ddot{\theta}_{skull}) = -k\theta_{brain} - c\dot{\theta}_{brain}$$

where I is the moment of inertia of the mass, k and c are the stiffness and damping values of the system, and $\theta_{brain}$ and $\theta_{skull}$ represent the angles of the brain (the mass) and the skull (the base).

In several embodiments, the brain angle metric computed is the maximum brain angle ($\vec{\theta}_{brain}$) in each anatomical direction. In many embodiments, the brain angle metric is a vector of the three peak brain angle values in each anatomical direction.

Returning back to FIG. 1, process 100 develops (105) a classifier to classify head impacts as a concussive or a non-concussive event based on the determined head kinematic metric. Accordingly, the head kinematic metric and head impact events are utilized to train a computational classifier to predict whether a concussive event occurred at impact. In some embodiments, the classifier is a regression model. Any appropriate regression model can be utilized, including (but not limited to) linear regression, logistic regression, elastic net regression, polynomial regression, stepwise regression, ridge regression, LASSO regression, and any combined regression models. Accordingly, in many embodiments, a regression model is trained to distinguish whether an impact was a concussive event (i.e., resulting in mTBI or concussion) or a non-concussive event. In many embodiments, the likelihood of a concussive event is fit to the following logistic model:

$$p_{injury} = (1 + e^{-\beta_0 - \Sigma \beta_i x_i})^{-1}$$

where $\beta_{injury}$ is the probability of concussive event, $x_i$ are the components of the injury criterion, and $\beta_i$ are the fitted coefficients, with i=1, 2, 3 representing the anatomical directions. In some embodiments, small sample bias is corrected, which may be of benefit when the datasets have a small number of concussive events.

In a number of embodiments, a risk curve of a concussive event is developed, which determines the percent likelihood that a head impact was a concussive event. In many embodiments, a threshold can be set to capture a specific percent risk that an impact was a concussive event, which can be changed based on specificity and sensitivity. For example, a threshold may be set to capture high sensitivity but may also result in detecting false-positive concussive events. The precise threshold would be dependent on the classifier developed and the sensitivity and/or specificity desired. In various embodiments, a threshold is set to capture at least 50%, 60%, 70%, 80%, 90%, 95%, or 99% of concussive events.

As shown in FIG. 1, a concussive event classifier can be integrated (107) into a system to be used in conjunction with a head-mounted device for real-time concussive injury detection. In many embodiments, the classifier and brain model is stored in memory of a computational device(s) that is in communication with a gyroscope, rotational accelerometer, and/or an array of linear accelerometers in association with a head-mounted device. In some embodiments, the head mounted device is in remote communication with a gyroscope, rotational accelerometer, and/or an array of linear accelerometers. Accordingly, during an impact, kinematic measurements can be acquired utilizing the head-mounted device to determine a brain angle metric via the brain model that is then used to determine whether a concussive event occurred via the classifier.

While specific examples of building a classifier to determine whether a concussive event occurred are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for building a classifier to determine whether a concussive event occurred appropriate to the requirements of a given application can be utilized in accordance with various embodiments of the invention.

Methods for Utilizing a Concussive Event Classifier

Multiple embodiments are also directed to utilizing a concussive event classifier for a medical assessment. Accordingly, many embodiments are directed to the use of a trained classifier utilizing mass kinematics to detect a concussive event in real time. In several embodiments, a brain model that measures brain angle motion in multiple degrees of freedom is utilized in conjunction with the trained classifier. In several embodiments, the brain model is a three degree-of-freedom, mass-spring damper model that models the rotational deformation of the brain from skull loading in the three anatomical directions (e.g., coronal, axial, and sagittal). In a number of embodiments, the brain model determines a brain angle metric. In many embodiments, the brain angle metric is a vector of the three peak brain angle values in each direction.

In several embodiments, a head kinematic metric is utilized in a concussive event classifier to determine that a concussive event occurred at impact. In some embodiments, the trained classifier is a regression model. Any appropriate trained regression model can be utilized, including (but not limited to) linear regression, logistic regression, elastic net regression, polynomial regression, stepwise regression, ridge regression, LASSO regression, and any combined regression models. In some embodiments, the regression model is trained to distinguish whether an impact was a concussive event (i.e., resulting in mTBI or concussion) or a non-concussive event. In numerous embodiments, data sets that include both concussive events and non-concussive events in which the kinematics were measured during the event are utilized to train the model. In some situations, kinematics can be measured by a gyroscope, rotational accelerometer, and/or an array of linear accelerometers associated with a head-mounted device.

Figure 2:
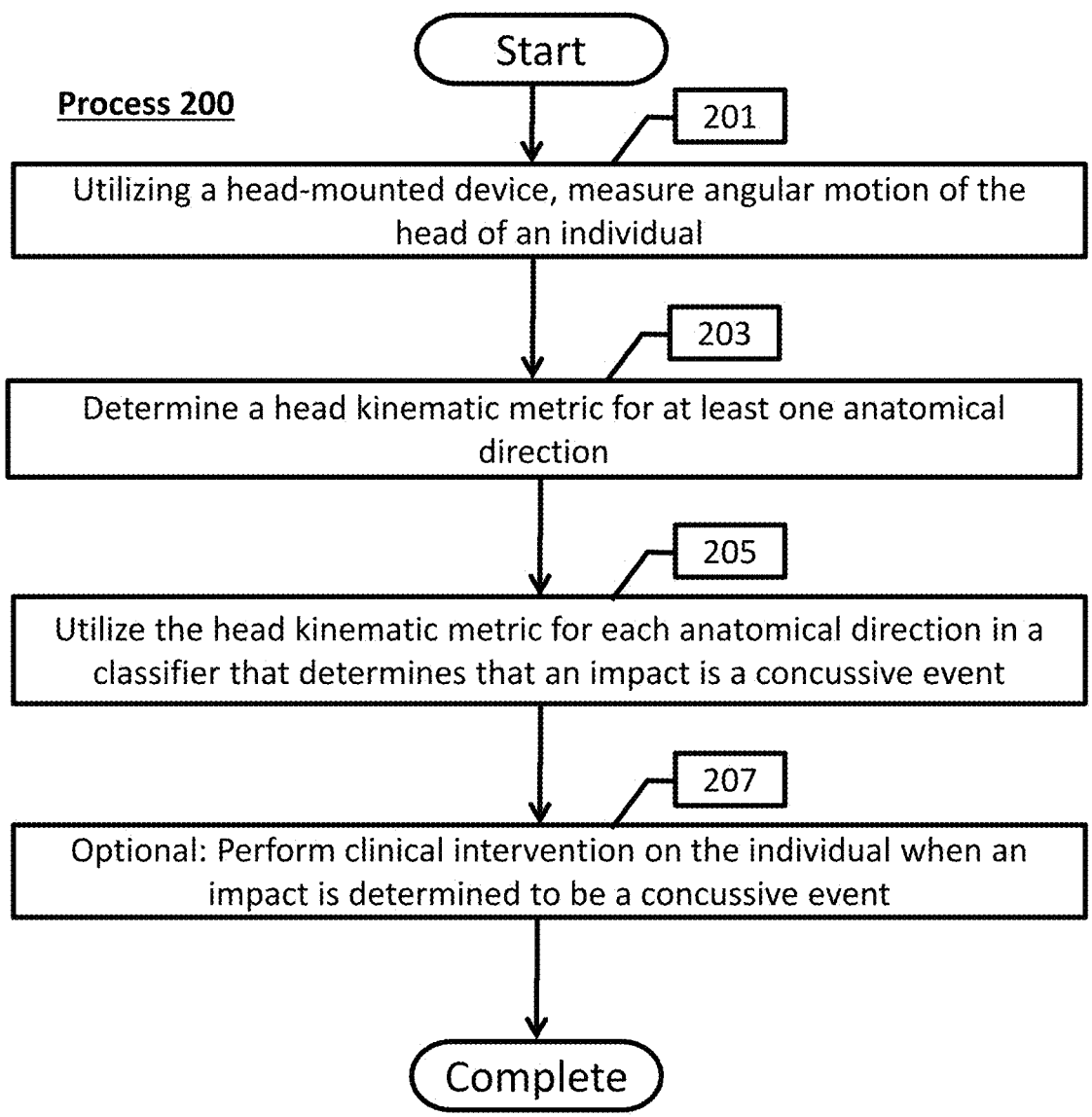
FIG. 2 provides a flow chart for utilizing a classifier to detect a concussive event in accordance with an embodiment.

Provided in FIG. 2 is an embodiment of a method to utilize a trained concussive event classifier for real-time detection of concussive injury. As shown in FIG. 2, process 200 begins by measuring (201) angular motion of the head of an individual utilizing a head-mounted device. In some embodiments, a head mounted device measures kinematics in multiple anatomical directions. Any appropriate device capable of measuring head motion can be utilized to capture data. In many embodiments, a gyroscope, rotational accelerometer, and/or an array of linear accelerometers in association with a head-mounted device is utilized to measure head kinematics. A head-mounted device can include (but not limited to) helmet, mouthguard, hat, ear protection, eye-wear, skin-mounted sensor, and head band.

Any appropriate kinematic measurements can be captured to compute a head kinematic. In several embodiments, kinetic measurements are utilized to determine the maximum brain angle in each anatomical direction. In many embodiments, kinematics are measured in three anatomical directions (e.g., coronal, axial, and sagittal).

As shown in FIG. 2, a head kinematic metric is determined (203) for at least one anatomical direction utilizing the obtained mass kinematic measurements. Any appropriate head kinematic metric can be utilized, including (but not limited to) peak angular acceleration ($\vec{\alpha}$), peak change in rotational velocity ($\Delta \vec{\omega}$), peak translational acceleration ($\vec{a}$), and a brain angle metric.

In embodiments, peak angular acceleration ($\vec{\alpha}$) is a vector defined as the maximum value of the rotational acceleration time series in each anatomical direction:

$$\vec{\alpha} = [\max|\alpha_x|\ \max|\alpha_y|\ \max|\alpha_z|].$$

Although three anatomical directions are shown (x, y, and z), it is to be understood that any appropriate number of anatomical directions can be utilized, and that at least one anatomical direction is utilized. In some embodiments, the maximum value is retrieved from the entire recorded time series for a given time series.

In embodiments, peak change in rotational velocity ($\Delta \vec{\omega}$) is defined as the largest change in rotational velocity magnitude in each anatomical direction:

$$\Delta \vec{\omega} = |\max \omega_x(t) - \min \omega_x(t)\ \max \omega_y(t) - \min \omega_y(t)\ \max \omega_z(t) - \min \omega_z(t)|.$$

Although three anatomical directions are shown (x, y, and z), it is to be understood that any appropriate number of anatomical directions can be utilized, and that at least one anatomical direction is utilized. In some embodiments, the maximum and minimum values for each component are retrieved from the entire recorded time series for a given series.

In embodiments, peak translational acceleration ($\vec{a}$) is defined as the peak absolute value of the translational acceleration vector time series in each anatomical direction:

$$\vec{a} = [a_x a_y a_z] = |\vec{a}(t)|,$$

Although three anatomical directions are shown (x, y, and z), it is to be understood that any appropriate number of anatomical directions can be utilized, and that at least one anatomical direction is utilized. In some embodiments, the maximum value is retrieved from the entire recorded time series for a given series.

In a number of embodiments, a mass-deformation brain model is utilized to compute a brain angle metric. Any appropriate mass-deformation brain model may be utilized, such as (for example) a mass-spring-damper model. In many embodiments, the mass-spring-damper brain model is a 3 degrees-of-freedom mechanical analog of the brain that measures brain angle in three anatomical directions (e.g., coronal, axial, and sagittal). In several embodiments, the brain model is developed assuming the brain has rigid-body motion behavior in each anatomical direction. Accordingly, in these embodiments, a separate mass-spring-damper system is used for each anatomical direction. In many embodiments, the mechanical mass-spring-damper system models the rotational deformation of the brain from skull loading. In some embodiments, the motion for each anatomical direction is computed as follows:

$$I(\ddot{\theta}_{brain} + \ddot{\theta}_{skull}) = -k\theta_{brain} - c\dot{\theta}_{brain}$$

where I is the moment of inertia of the mass, k and c are the stiffness and damping values of the system, and $\theta_{brain}$ and $\theta_{skull}$ represent the angles of the brain (the mass) and the skull (the base).

In several embodiments, the mass-deformation brain model is used to determine a brain angle metric. In some embodiments, the brain angle metric is the maximum brain angle ($\vec{\theta}_{brain}$) in each anatomical direction. In many embodiments, the brain angle metric is a vector of the three peak brain angle values in each anatomical direction.

Returning back to FIG. 2, process 200 utilizes (205) the head kinematic metric for each anatomical direction in a trained classifier to determine that an impact is a concussive event. In some embodiments, the classifier is a regression model. Any appropriate regression model can be utilized, including (but not limited to) linear regression, logistic regression, elastic net regression, polynomial regression, stepwise regression, ridge regression, LASSO regression, and any combined regression models. In many embodiments, the regression model was trained to distinguish whether an impact was a concussive event (i.e., mTBI or concussion) or a non-concussive event. In many embodiments, the likelihood of a concussive event was fit to the following logistic model:

$$p_{injury} = (1+e^{-\beta_0 - \Sigma \beta_i x_i})^{-1}$$

where $p_{injury}$ is the probability of concussive event, $x_i$ are the components of the injury criterion, and $\beta_i$ are the fitted coefficients, with i=1, 2, 3 representing the anatomical directions. In some embodiments, small sample bias was corrected, which may be of benefit when the datasets used for training have a small number of concussive events.

In a number of embodiments, a risk curve of a concussive event has been developed, which determines the percent likelihood that a head impact was a concussive event. In many embodiments, a threshold is set to capture a specific percent risk that an impact was a concussive event, which can be changed based on specificity and sensitivity. For example, a threshold may be set to capture high sensitivity but may also result in detecting false-positive concussive events. The precise threshold would be dependent on the classifier developed and the sensitivity and/or specificity desired. In various embodiments, a threshold is set to capture at least 50%, 60%, 70%, 80%, 90%, 95%, or 99% of concussive events.

In several embodiments, feedback and/or an alert is signalled with the indication of whether a concussive event has occurred as determined by the computational classifier. In some embodiments, the feedback and/or alert is signalled in real-time.

As shown in FIG. 2, process 200 can optionally perform (207) a medical intervention on the individual when an impact is determined to be a concussive event. A medical intervention is a medical procedure or treatment to be performed on the individual. Medical procedures include (but note limited to) assessing the individual's symptoms and performing various concussion examinations (e.g., field test, neurological assessment, medical imaging, and observation). Treatments include (but not limited to) physical and mental rest, and pain relief and anti-inflammatory medicine.

While specific examples of utilizing a classifier to determine whether a concussive event occurred are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for utilizing a classifier to determine whether a concussive event occurred appropriate to the requirements of a given application can be utilized in accordance with various embodiments of the invention.

Systems and Devices for Detecting a Concussive Event

Various embodiments are directed to systems and devices for detecting a concussive event utilizing a concussive event classifier. In several embodiments, systems and devices detect head motion, measure mass kinematic data, compute a head kinematic metric, and/or determine that a concussive event occurred. Numerous modalities may be utilized to implement detection of a concussive event. In many embodiments, a head-mounted device is utilized to detect head motion and measure mass kinematics utilizing a gyroscope, rotational accelerometer, an array of linear accelerometers, and/or other similar motion detection components.

In several embodiments, a computing system computes a brain angle metric and/or determines that a concussive event occurred.

Figure 3:
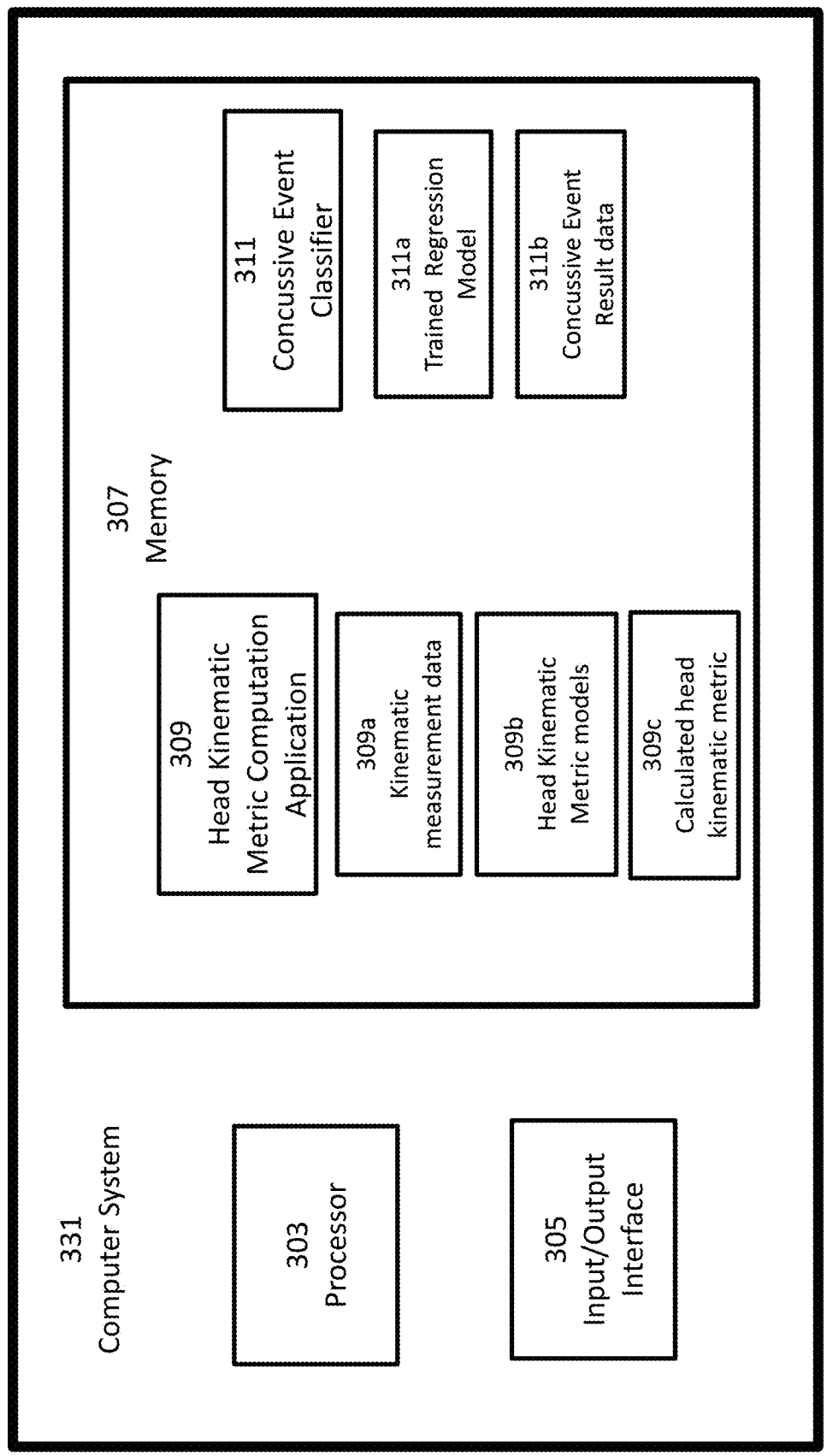
FIG. 3 provides a schematic for a computational system to classify head impacts in accordance with an embodiment.

Turning now to FIG. 3, a computing system (301) may be implemented on a single or a plurality of intercommunicative computing device(s) in accordance with some embodiments of the invention. The computing system (301) may be any computing device with sufficient processing power, or any plurality and/or combination of computing devices for the processes described herein. The computing system may be incorporated within, proximal to, or in remote communication with a head-mounted device capable of measuring head motion. The computing system (301) includes a processor (303), which may refer to one or more devices within the computing system (301) that can be configured to perform computations via machine readable instructions stored within a memory (307) of the computer system (301). The processor may include one or more microprocessors (CPUs), one or more graphics processing units (GPUs), and/or one or more digital signal processors (DSPs).

In a number of embodiments of the invention, the memory (307) may contain a head kinematic metric computation application (309) and a concussive event classifier (311) that performs all or a portion of various methods according to different embodiments of the invention described throughout the present application. As an example, the processor (303) may perform a concussive event detection method similar to any of the processes described above with reference to FIG. 2, during which memory (307) may be used to store various intermediate processing data such as kinematic measurement data (309a), head kinematic metric models (309b), calculated head kinematic metric (309c), trained regression model (311a), and concussive event result data (311b).

In some embodiments of the invention, the computer system (301) may include an input/output interface (305) that can be utilized to communicate with a variety of devices, including (but not limited to) a head-mounted device, other computing systems, a projector, and/or other display devices. As can be readily appreciated, a variety of software architectures can be utilized to implement a computer system as appropriate to the requirements of specific applications in accordance with various embodiments of the invention.

Although computer systems and processes for detecting a concussive event are described above with respect to FIG. 3, any of a variety of devices and processes for data associated with detection of a concussive event as appropriate to the requirements of a specific application can be utilized in accordance with many embodiments of the invention.

In numerous embodiments, a computer system is in communication with a head-mounted device that incorporates components that measure head motion (e.g., gyroscope, accelerometer). Accordingly, head kinematic data is measured by a head-mounted device and is communicated to the computing system. In some embodiments, a computer system is incorporated within a head-mounted device. In some embodiments, a computer system is remote from a head-mounted device. The computing system determines whether a concussive event occurs in real-time. In some embodiments, an output interface signals that a concussive event has occurred. Any appropriate signal may be utilized, such as (for example) a message, a visual cue, or an audible cue. In some embodiments, kinematic data, calculated brain metrics, and concussive event data are stored within the computational system, which may be retrieved at a later time.

Head mounted devices in communication with a computational system include but not limited to) helmet, mouthguard, hat, ear protection, eye-wear, skin-mounted sensor, and head band.

Clinical Applications

Various embodiments are directed towards utilizing detection of a concussive event to perform medical interventions. In a number of embodiments, an individual wears a head-mounted device to monitor for a concussive event. When a concussive event is detected, a clinical intervention can be performed. Medical interventions include medical procedures and treatments. Medical procedures include (but not limited to) assessing the individual's symptoms and performing various concussion examinations (e.g., field test, neurological assessment, medical imaging, and observation). Treatments include (but not limited to) physical and mental rest, and pain relief and anti-inflammatory medicine. In some embodiments, an individual is assessed and/or treated by medical professional, such as a doctor, nurse, medical trainer, emergency medical technician (EMT) or similar.

Detection of Concussive Event for Medical intervention

In several embodiments as described herein a concussive event can be detected utilizing a head-mounted device in communication with a computing system with a concussive event classifier. In many embodiments, a concussive event is detected when a kinematic head metric at impact is greater than a threshold. In numerous embodiments, a regression model is utilized to determine whether an impact is a likely concussive event. Accordingly, in a number of embodiments, a head-mounted device detects head motion, and computing systems utilize kinematic measurements to compute a head kinematic metric and/or determine that a concussive event occurred. This process is especially useful in a field setting to provide a real-time determination of a concussive event.

An exemplary procedure for a detecting a concussive event is as follows:
 a. measure head kinematics via head-mounted device
 b. compute a head kinematic metric
 c. determine that an individual suffered a concussive event
 d. perform medical intervention based on the determination that the individual suffered a concussive event In a number of embodiments, occurrence of a concussive event is detected in real time. In some embodiments, individuals at risk of concussive event wear a head-mounted device to measure head kinematics. Individuals at risk of a concussive event include (but not limited to) athletes, fighters, military personnel, epileptics, or anyone at risk of a head injury. Based on the occurrence of a concussive event, a medical procedure and/or treatment may be performed.

Diagnostics and Treatments

A number of embodiments are directed towards detecting that a concussive event occurred in an individual and then based on the event occurring, performing further medical procedures and/or treating the individual.

In accordance with several embodiments, once a concussive event is detected, a number of follow-up diagnostic procedures can be performed, including (but not limited to) field test, neurological assessment, cognitive testing, medical imaging, and observation. Field tests include (but not limited to) Glasgow coma scale, standardized assessment of concussion (SAC), sport concussion assessment tool (SCAT), military acute concussion evaluation, King-Devick test, clinical reaction time test, balance error scoring system (BESS), and sensory organization test (SOT) (see R. Graham, F. P. Rivara, M. A. Ford, and C. M. Spicer SPORTS-RELATED CONCUSSIONS IN YOUTH: IMPROVING THE SCIENCE, CHANGING THE CULTURE Washington (DC): National Academies Press (US); (2014), pp. 309-316, the disclosure of which is incorporated herein by reference). Neurological assessment involves examination of vision, hearing, strength, sensation, coordination, and reflexes. Cognitive testing involves evaluation of memory, concentration, and ability to recall information. Medical imaging includes (but is not limited to) X-ray, magnetic resonance imaging (MRI), and computed tomography (CT). Observation may include surveillance by a medical professional for a period of time (e.g., 1 hour, 2 hours, 4 hours, 12 hours, 24 hours).

In accordance with many embodiments, once a concussive event is detected, a number of treatments can be performed, including (but not limited to) physical and mental rest, and pain relief and anti-inflammatory medicine. Pain relief and anti-inflammatory medicine includes (but not limited to) acetaminophen and nonsteroidal anti-inflammatory drugs (e.g., aspirin, ibuprofen, naproxen).

EXEMPLARY EMBODIMENTS

The following sections set forth certain selected embodiments related to the above disclosure. It will be understood that the embodiments presented in this section are exemplary in nature and are provided to support and extend the broader disclosure, these embodiments are not meant to confine or otherwise limit the scope of the invention.

Example 1: Multi-Directional Dynamic Model for Traumatic Brain Injury Detection

Given the worldwide adverse impact of traumatic brain injury (TBI) on the human population, its diagnosis and prediction are of utmost importance. Historically, many studies have focused on associating head kinematics to brain injury risk. Recently, there has been a push towards using computationally expensive finite element (FE) models of the brain to create tissue deformation metrics of brain injury. Here, a new brain injury metric, the Brain Angle Metric (BAM), was developed based on the dynamics of a 3 degree-of-freedom lumped parameter brain model. The brain model is built based on the measured natural frequencies of an FE brain model simulated with live human impact data. The model can be used to rapidly estimate peak brain strains experienced during head rotational accelerations that cause mild TBI. The model correlates with peak principal FE strain ($R^2$=0.82). Further, coronal and axial brain model displacement correlated with fiber-oriented peak strain in the corpus callosum ($R^2$=0.77). The injury metric BAM uses the maximum angle predicted by the brain model and is compared against a number of existing rotational and translational kinematic injury metrics on a dataset of head kinematics from 27 clinically diagnosed injuries and 887 non-injuries. It was found that BAM performed comparably to peak angular acceleration, translational acceleration, and angular velocity in classifying injury and non-injury events. Metrics which separated time traces into their directional components had improved model deviance to those which combined components into a single time trace magnitude.

Introduction

In the mid-20th century, rising motor vehicle and sporting deaths led to the establishment of safety standards that targeted reduction of forces that deform or fracture the skull. In the 1960's, the Wayne State University tolerance threshold[8] was developed, motivating two translational acceleration standards: the Gadd severity index (SI)[9] and Head Injury Criterion (HIC) (for more the Wayne State University tolerance threshold, see Gurdjian, E. S., Roberts, V. L., and Thomas, L. M. (1966). *J. Trauma* 6, 600-604; for more on the Gadd SI, see Gadd, C. W. (1966). Proc. 10th Stapp Car Crash Conferfence, *SAE Pap. No.* 660793 SAE Paper, 164-174; and for more on the HIC, see Occupant Crash Protection—Head Injury Criterion. Dep. Transp. NHTSA Docket Number 69-7, Not. 19; the disclosures of which are each incorporated herein by reference). The two biggest regulating bodies for enforcing safety standards, the National Highway Traffic Safety Administration (NHTSA) and National Operating Committee on Standards for Athletic Equipment (NOCSAE), still evaluate injury risk based on translational acceleration (see Occupant Crash Protection—Head Injury Criterion. Dep. Transp. NHTSA Docket Number 69-7, Not. 19; and National Operating Committee on Standards for Athletic (NOCSAE) (2012) Standard performance specification for newly manufactured football helmets—NOCSAE 002; the disclosures of which are each incorporated herein by reference). NHTSA uses a metric based on the time history of translational head acceleration as the only federally-mandated head injury metric in automobile safety regulation, whereas NOCSAE uses a maximum resultant translational acceleration criterion to evaluate helmet design. Despite widespread use of translation-based metrics to predict head injury, these metrics are not suitable for assessing all types of brain injury.

Diffuse brain injury, which can occur through purely inertial head acceleration even in the absence of skull deformation, has become better understood since the development of HIC and SI. Rapid head rotations can shear and deform the white matter of the brain causing diffuse axonal injury (DAI), a fundamentally different injury than focal injuries caused by skull deformation which are primarily caused by translational motions. Indeed, while head translational acceleration is an important factor for focal trauma such as skull fracture, rotational acceleration causes time-dependent inertial loading of the brain and better correlates with brain trauma severity in animal experiments. More recently, NHTSA developed the brain injury criterion (BrIC) to predict TBI risk by relating head rotational velocity to critical brain strains; this criterion has been proposed to be used in the New Car Assessment Programs rating (Takhounts, E. G., Craig, M. J., Moorhouse, K., Mcfadden, J., and Hasija, V. (2013). *Stapp Car Crash J.* 57, 1-24, the disclosure of which is incorporated herein by reference). Realizing that both translational and rotational head kinematics may factor into injury risk, some 6 degree-of-freedom (DOF) criteria such as head impact power (HIP) and generalized acceleration model for brain injury threshold (GAMBIT) have also been developed, which include both translational and rotational components of acceleration. Brain tissue deformation metrics calculated from finite element (FE) simulations are another category of frequently investigated injury criteria (for more HIP, see Newman, J. A., Shewchenko, N., and Welbourne, E. (2000) *Stapp Car Crash J.* 44, 362; for more on GAMBIT, see Newman, J. (1986). *Proc. Int. Res. Counc. Biokinetics Impacts,* 121-131; the disclosures of which are each incorporated herein by reference). Using these FE models, researchers simulate metrics such as tissue strain and strain rate to predict injury risk. Morphologically-based metrics such as fiber tract-oriented strain, which better accounts for anisotropy in brain tissue, have also been found to correlate with injury (see Sahoo, D., Deck, C., and Willinger, R. (2016). *Acid. Anal. Prev.* 92, 53-70, the disclosure of which is incorporated herein by reference). Although finite element model-derived criteria provide more physical intuition behind injury risk prediction than skull-kinematics based criteria, they are severely limited by long computational running time and may not be practical options as federal standards.

Simplified mechanical models of the brain have been developed and used to gain insight into brain tissue deformation since the 1950's, when Kornhauser first investigated the sensitivity of mass-spring systems to transient accelerations in the context of brain injury. Since then, both rotational and translational lumped-parameter brain models have been developed to better understand how the brain deforms under head acceleration; however, many of these models were not effectively validated due to lack of experimental data. More recently, with the development of validated FE brain models, there have been efforts towards developing simplified, linear mechanical analogs of these brain FE models. Gabler et al. developed a mass-spring-damper lumped model of the brain, fitting parameters to match mass displacement to maximum principal strain from brain FE models over a range of idealized force profiles applied to the skull (Gabler, L. F., Joodaki, H., Crandall, J. R., and Panzer, M. B. (2018). *J. Biomech. Eng.* 140, 31002, the disclosure of which is incorporated herein by reference). Gabler et al. found that the peak principal strain from FE models can be adequately reproduced using simple mechanical systems.

To identify promising injury criteria for predicting human injury risks, the ideal approach is to compare the performance of all candidate injury criteria with a large human injury and non-injury dataset. However, only a small number of studies have compared different injury criteria using a common dataset. In a previous study, injury criteria were evaluated using a six degrees of freedom (6DOF) human injury dataset containing two injuries (see F. Hernandez, et al., (2015). *Ann. Biomed. Eng.,* 43, 1918-1934, the disclosure of which is incorporated herein by reference). These results helped provide insight into promising injury criteria, showing the importance of rotational measurements for predicting injury. However, the scarcity of full 6DOF human injury data has hindered the ability to make statistically significant comparisons of all injury criteria. In addition, because of the relative infrequency of concussions compared to non-concussive impacts, existing datasets are typically biased and injury functions are developed using similar numbers of injuries and non-injuries, with few studies considering injury risk variations with sampling variability and sampling bias.

In this example, a three degree-of-freedom, mass-spring-damper model of the brain was developed, with parameters based on modal analysis of brain displacements due to real-world impacts. This approach is contrary to previous approaches of fitting lumped model parameters to FE simulation results using idealized pulses. Described herein is the Brain Angle Metric (BAM), a metric for classifying between injurious and non-injurious impacts. BAM was compared to several existing injury criteria, using a combined 6DOF human head kinematics dataset from multiple loading regimes.

Materials and Methods

Head Kinematics Datasets

In this study, human male injury and non-injury datasets from multiple loading regimes were included, as listed in Table 1. Each datapoint of the dataset included if either 1) all 6DOF head kinematics were available, or 2) the head motion protocol was mainly constrained to a single plane and in that plane were available. For datapoints of case 2, all head motion outside of the single recorded plane was set to random noise with magnitude less than 10% of the peak value in the recorded plane of motion to account for small out of plane movements. Using these criteria, data were included from the following experiments. Wu et al. measured head impact kinematics during football practice and game events with instrumented mouthguards ($n_{injury}$=0, $n_{noninjury}$=139) (L. Wu, et al., (2017) Scientific reports, 8, 855, the disclosure of which is incorporated herein by reference). Hernandez et al. measured head impact kinematics during athletic events using instrumented mouthguards ($n_{injury}$=2, $n_{noninjury}$=535) (F. Hernandez, et al., (2015), cited supra). More recently, a single concussive impact was recorded using the Stanford Mouthguard in high school football using the same measurement protocols as described by Hernandez et al ($n_{injury}$=1, $n_{noninjury}$=0). Together, these three datasets constitute the Stanford mouthguard (MG).

The following studies included all the necessary 6DOF measurement data in the datasets. Hernandez et al. measured head kinematics during rapid voluntary head rotations using instrumented mouthguards ($n_{injury}$=0, $n_{noninjury}$=29) (F. Hernandez and D. B. Camarillo, (2018) J. Neurotrauma 11, neu.2016.4758, the disclosure of which is incorporated herein by reference). O'Keeffe et al. measured head kinematics from four mixed martial arts (MMA) fighters who received clinically-diagnosed concussions ($n_{injury}$=4, $n_{noninjury}$=0) (E. O'Keefe, et al., (2019) J. Neurotrauma (epub), the disclosure of which is incorporated by reference). Pellman et al. reconstructed injury and non-injury NFL head impacts by video analysis and dummy models (E. J. Pellman, et al., (2003) Neurosurgery 53,796, the disclosure of which is incorporated herein by reference). However, the data from this original publication was found to be erroneous due to a faulty accelerometer and has since been reanalyzed and corrected by Sanchez et al. ($n_{injury}$=20, $n_{noninjury}$=33) (E. J. Sanchez, et al., (2019), Clinical biomechanics, 64, 82-89, the disclosure of which is incorporated herein by reference).

In addition, within the following three studies, the head motion was mainly constrained to a single plane. Ewing et al. performed three studies using non-injury sled tests on Navy volunteers in the coronal and sagittal directions ($n_{injury}$=0, $n_{noninjury}$=151) (C. L. Ewing, et al., (1976) SAE Tech. Pap. 760800; C. L. Ewing (1975) The Effect of the Initial Position of the Head and Neck on the Dynamic Response of the Human Head and Neck to −Gx Impact Acceleration. pps. 487-512; and C. Ewing, (1978) SAE Tech. Pap. 780888, 3151-3165; the disclosures of which are each incorporated herein by reference). In total, 27 injury data points and 887 non-injury data points were utilized for analysis. Injury cases were defined to be cases in which there was a clinical diagnosis of concussion from a physician. For more information on head kinematics measurements, refer to Supplementary Materials Section.

All the listed datasets contain measurements of translational acceleration and rotational velocity. The Wu and Hernandez athletic data were recorded at 1000 Hz for a duration of 100 ms. The Hernandez voluntary motion data were recorded at 1000 Hz for 500 ms. The O'Keefe data were recorded at 1000 Hz for a duration of 200 ms. The sampling frequency of the Navy volunteer data and NFL reconstruction data were not reported, and the duration varied between 50 and 300 ms. All the data were projected to the center of gravity of the head and rotated to anatomical axes (x—anterior/posterior translation and coronal rotation, y—left/right translation and sagittal rotation, z—inferior/superior translation and axial rotation). The translational acceleration data were filtered at the CFC180 filter of 300 Hz, and the angular velocity data were filtered at the lowest sensor bandwidth of 184 Hz.

TABLE 1

Kinematics expressed in mean and standard deviation values from different data sources.

| Authors | Year | Description | Sample size (injured) | Lin. Accel. (g) | | |
|---|---|---|---|---|---|---|
| | | | | Lateral | Ant-Post | Inf-Sup |
| Wu et al. [23] | 2016 | Collegiate Football | 139 (0) | 15.4 ± 9.6 | 17.0 ± 14.3 | 11.1 ± 9.3 |
| Hernandez et al. [24] | 2014 | Collegiate Football | 537 (2) | 16.1 ± 13.5 | 12.3 ± 10.6 | 13.8 ± 15.4 |
| Sanchez et al. [25] | 2003 | NFL Football | 53 (20) | 53.9 ± 33.2 | 35.2 ± 18.9 | 29.4 ± 13.4 |
| see Supplementary | 2019 | High school football | 1 (1) | 12.2 | 5.9 | 31.2 |
| Ewing et al. [26] | 1976 | Navy sled tests | 51 (0) | 18.2 ± 1.3 | 17.9 ± 1.2 | 17.9 ± 1.2 |
| Ewing et al. [27] | 1975 | Navy sled tests | 100 (0) | 18.3 ± 1.8 | 18.1 ± 1.3 | 17.9 ± 0.8 |
| Hernandez et al. [28] | 2018 | Voluntary motion | 29 (0) | 25.0 ± 10.5 | 32.3 ± 9.2 | 21.6 ± 9.7 |
| OKeeffe et al. [29] | 2019 | Mixed martial arts | 4 (4) | 106.4 ± 82 | 50.2 ± 44 | 116.7 ± 94 |

| Authors | Year | Rot. Accel. (rad/s$^2$) | | | Rot. Vel (rad/s) | | |
|---|---|---|---|---|---|---|---|
| | | Coronal | Sagittal | Axial | Coronal | Sagittal | Axial |
| Wu et al. [23] | 2016 | 1464.8 ± 1940.5 | 830.9 ± 1015.7 | 664.3 ± 483.2 | 7.5 ± 5.4 | 7.6 ± 4.1 | 6.5 ± 4.0 |
| Hernandez et al. [24] | 2014 | 670.7 ± 872.5 | 1091.9 ± 1403.1 | 543.6 ± 487.1 | 6.4 ± 4.5 | 9.3 ± 6.8 | 6.5 ± 4.4 |
| Sanchez et al. [25] | 2003 | 2593.5 ± 1734.0 | 1890.4 ± 1088.1 | 2202.9 ± 1643.1 | 24.8 ± 11.3 | 12.6 ± 6.7 | 16.6 ± 12.7 |
| see Supplementary | 2019 | 2189 | 4922 | 1651 | 48.9 | 96.2 | 66.5 |
| Ewing et al. [26] | 1976 | 827.8 ± 365.6 | 199.9 ± 0.1 | 199.9 ± 0.1 | 16.5 ± 8.0 | 1.2 ± .04 | 1.3 ± 0.6 |
| Ewing et al. [27] | 1975 | 199.9 ± 0.1 | 773.6 ± 349.6 | 199.9 ± 0.1 | 1.1 ± 0.5 | 15.5 ± 7.6 | 1.0 ± 0.4 |
| Hernandez et al. [28] | 2018 | 103.1 ± 51.4 | 54.9 ± 23.1 | 211.4 ± 121.2 | 4.8 ± 3.9 | 2.0 ± 1.0 | 11.3 ± 7.1 |
| OKeeffe et al. [29] | 2019 | 5381 ± 2973 | 11522 ± 8030 | 9969 ± 9153 | 15.0 ± 3.6 | 36.0 ± 26 | 19.8 ± 14 |

Brain Finite Element (FE) Modeling

Figure 4:
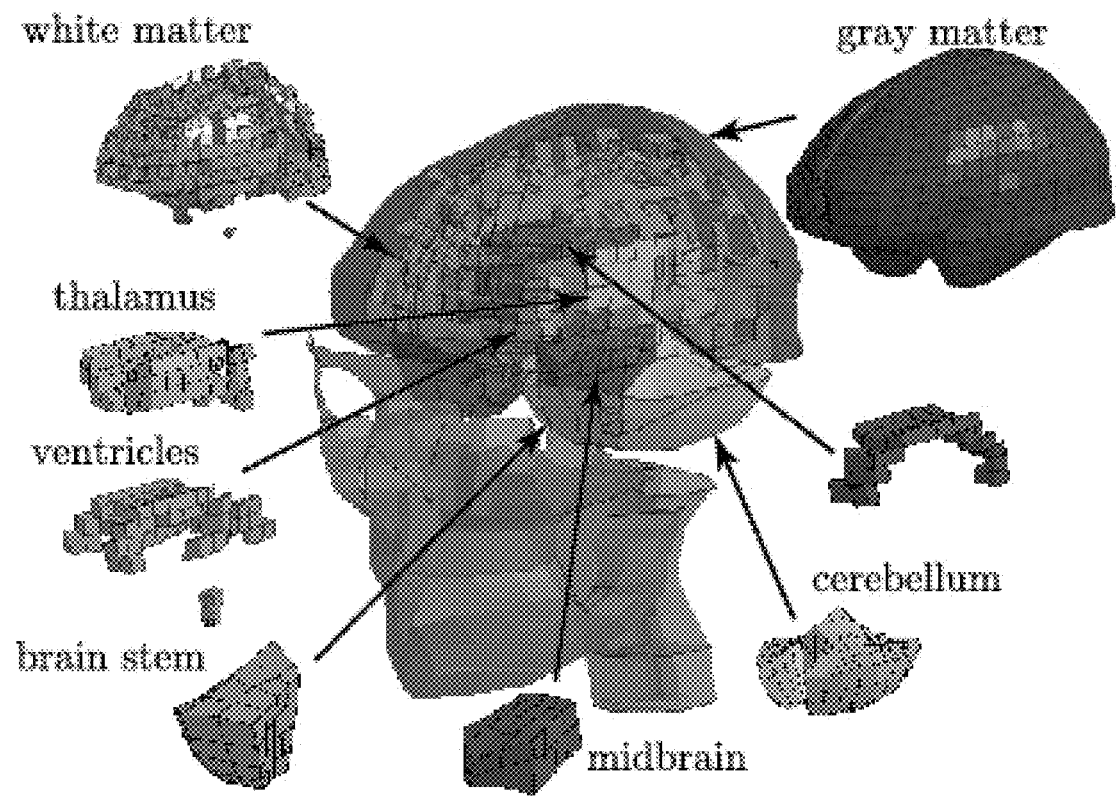
FIG. 4 provides a schematic for an isotropic brain finite element model in accordance with the prior art.
Figure 5:
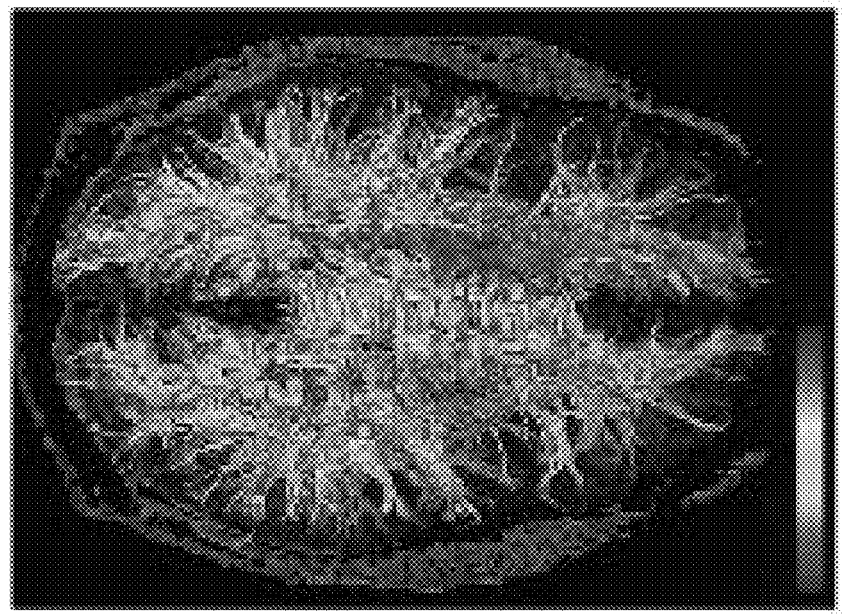
FIG. 5 provides a brain anisotropy diagram of in accordance with the prior art.
Figure 5:
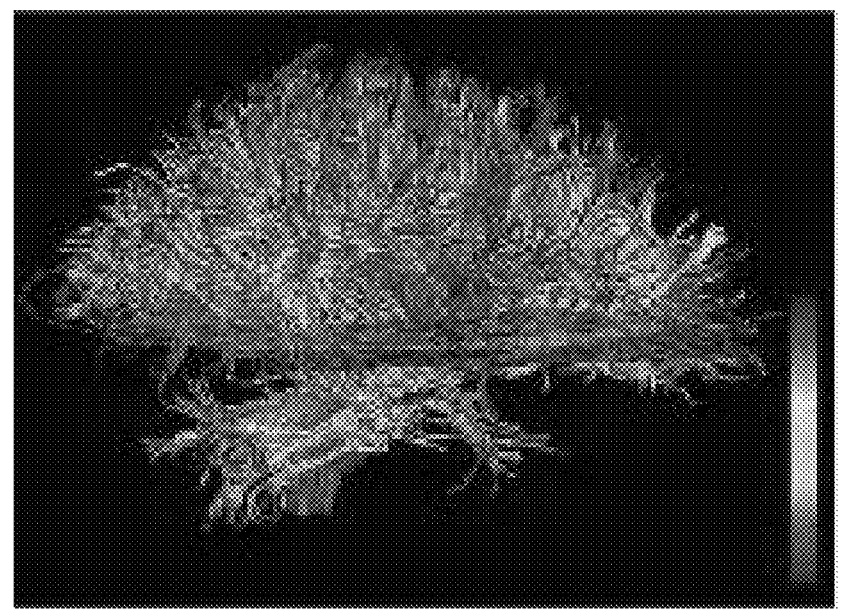

To calculate local brain tissue deformations resulting from head impacts, head impacts were simulated using a validated FE head model developed at the KTH Royal Institute of Technology (Stockholm, Sweden), which represents an average adult male human head (FIG. 4) (S. Kleiven (2007) Stapp Car Crash J. 51, 81-114, the disclosure of which is incorporated herein by reference). Due to computational cost of running FE simulations, only a subset of the American football head impacts with higher kinematics were simulated. All impacts from the NFL dataset were simulated. Within the Stanford MG dataset, a total of 188 cases using the newly developed FE model were simulated, including all the impacts resulting in a clinically diagnosed concussion. Further, all impacts in which the peak value of at least one translational or rotational component exceeded that of any of the three clinically diagnosed concussions recorded by the Stanford MG were simulated, along with a random sample of 10% of the remaining impacts. The FE-simulated impacts were thus biased towards higher severity impacts that would be most difficult to classify for a machine learning classifier. For these simulations, the measurements of skull translational accelerations and rotational velocities were used as input to the model and simulate the entire duration of the impact. From the simulations, two commonly-used deformation metrics were computed: peak principal strain in the brain and 15% cumulative strain damage metric (CSDM). Peak principal strain is the maximum strain among any element over the entire time trace. CSDM represents the cumulative volume of the brain matter experiencing strains over a critical level of 15%. Lastly, the peak axonal strain was calculated in the corpus callosum, because the strain along the axonal fiber tracts may correlate well with injury risk (FIG. 5). To do this, the tissue strain in the brain was projected along the fiber tract directions, and took the maximum value experienced within the corpus callosum.

Lumped Parameter Brain Model

Figure 6:
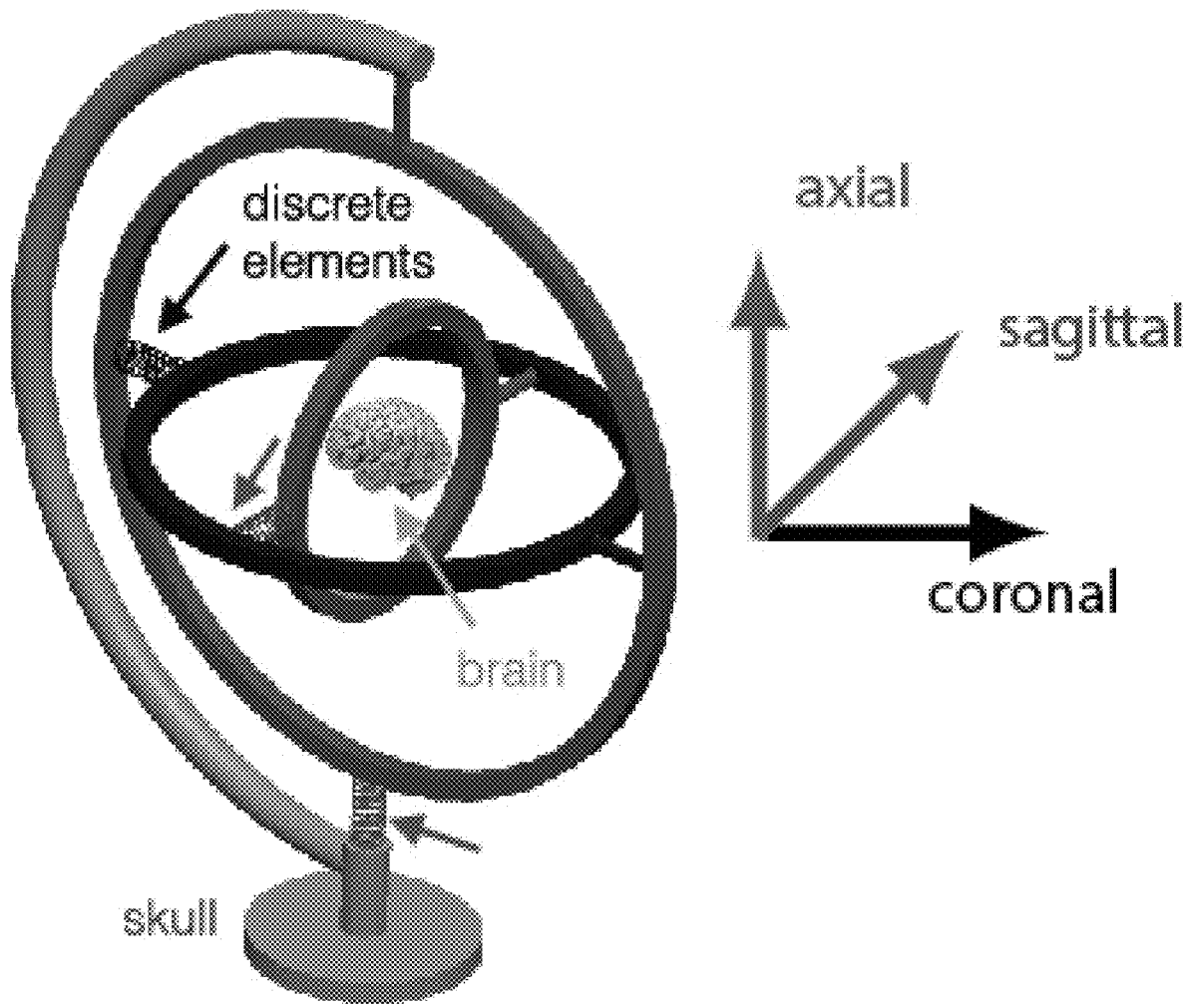
FIG. 6 provides a schematic of a diagram of a three-dimensional lumped parameter brain model in accordance with an embodiment of the invention.

Although brain tissue and the brain-skull interface exhibit nonlinear viscoelastic behavior, this complex relationship can be simplified through linear mechanical elements. Here, a new lumped parameter brain model was developed by creating a 3 DOF mechanical analog of the brain as follows: a rigid-body behavior was assumed for the brain's motion in three anatomical directions and therefore used three separate spring-damper systems attached to the mass of the brain (FIG. 6). This mechanical mass-spring-damper system models the rotational deformation of the brain from skull loading. To model accelerations of the skull, an input was applied as an excitation to the base of the system. The equation of motion for this system are as follows:

$$I(\ddot{\theta}_{brain}+\ddot{\theta}_{skull})=-k\theta_{brain}-c\dot{\theta}_{brain}$$

where I is the moment of inertia of the mass, k and c are the stiffness and damping values of the system, and $\theta_{brain}$ and $\theta_{skull}$ represent the angles of the brain (the mass) and the skull (the base). Previously reported moments of inertia and dynamics parameters (dominant frequency [$\omega_x$, $\omega_y$, $\omega_z$] and decay rate [$\lambda_x$, $\lambda_y$, $\lambda_z$]) were assigned in each anatomical direction (K. Laksari, et al. (2018) Phys. Rev. Lett., 120, 138101, the disclosure of which is incorporated herein by reference). Inertia values for a 50$^{th}$ percentile male brain of I=[0.016, 0.024, 0.022] kgm$^2$ were used for coronal, sagittal and axial directions respectively, and derived the corresponding spring and damper coefficients using the following relationships:

$$\omega_n = \sqrt{\frac{k}{I}}, \quad \lambda_{x,y,z} = -\frac{c_{x,y,z}\omega_n}{2\sqrt{k_{x,y,z}I_{x,y,z}}}, \quad \omega_{x,y,z} = \omega_n\sqrt{1-\left(\frac{\lambda_{x,y,z}}{\omega_n}\right)^2}$$

Table 2 lists model parameters in each anatomical direction. Each impact was simulated using the lumped parameter model by applying the angular skull kinematics to the base of the mass spring damper system. For each impact, measured time traces in each anatomical direction were applied to the corresponding mass-spring-damper model. This resulted in a vector of the three peak relative brain angle values in each direction ($\vec{\theta}_{brain}$).

With the tissue deformation metrics calculated from the FE simulations of the KTH model brain, a linear regression was run between the maximum resultant brain angle ($\theta_{brain}^r$) and peak principal strain, and between $\theta_{brain}^r$ and CSDM. Additionally, a multi-dimensional linear regression was run of maximum $\vec{\theta}_{brain}$ in each direction with tract-oriented corpus callosum strain.

TABLE 2

Parameters used in mass-spring-damper brain model.

| Anatomical direction | x | y | z |
|---|---|---|---|
| Moment of inertia (kgm$^2$) | 0.016 | 0.024 | 0.022 |
| Decay rate (1/s) | −32 | −38 | −30 |
| Natural frequency (Hz) | 22 | 22 | 25 |
| Spring stiffness (Nm/rad) | 322.1 | 493.2 | 562.6 |
| Damper viscosity (Nms/rad) | 1.024 | 1.824 | 1.320 |

Brain Injury Metric Analysis

Having shown the correlation of the brain angle measures with local tissue and axon deformations, the maximum brain angle ($\vec{\theta}_{brain}$) was used in each anatomical direction as a new brain injury metric, the Brain Angle Metric (BAM). Further, the performance of BAM was compared against other existing injury criteria. Using the kinematics data, the following rotational kinematics-based injury criteria was computed: peak rotational acceleration in each direction ($\vec{\alpha}$), peak resultant rotational acceleration ($\alpha_r$), peak change in rotational velocity in each direction ($\vec{\Delta\omega}$), peak resultant change in rotational velocity ($\Delta\omega_r$), brain injury criterion (BrIC), and rotational injury criterion (RIC). Translational kinematics-based injury criteria was also computed: peak translational acceleration in each direction ($\vec{a}$), peak resultant translational acceleration ($a_r$), HIC$_{15}$, HIC$_{36}$, and Gadd Severity Index (SI). Lastly, injury criteria that take into account both rotation and translation was included: the 6DOF head impact power (HIP), HIP separated into each direction (HIP$_{3D}$), generalized acceleration model for brain injury threshold (GAMBIT), and the Virginia Tech combined probability metric (VTCP). For more detailed information about each criterion, refer to the Supplementary Materials Section.

Since the injury and non-injury data likely fall in a binomial distribution, a logistic regression model was fit for each kinematic injury criteria on the full dataset of injuries and non-injuries. In order to understand the ability of the BAM metric to predict injuries compared to the FE results, a logistic regression model was also fit on a smaller subset of just the football head impacts for strain-based criteria. the logistic model to each injury criterion was fit using the following equation, $p_{injury}=(1+e^{-\beta_0-\Sigma\beta_i x_i})^{-1}$, where $p_{injury}$ is the probability of injury, $x_i$ are the components of the injury criterion, and $\beta_i$ are the fitted coefficients, with i=1, 2, 3 representing the anatomical directions. The following performance measures were computed and compared to assess the predictive value of each injury criterion. The deviance (D) statistic given by $$D = -2\ln\left(\frac{\text{likelihood of the fitted model}}{\text{likelihood of saturated model}}\right)$$

assesses the quality of fit of a logistic regression (analogous to $R^2$ in linear regression) and has been used to assess mTBI prediction (also known as −2LLR). For each model, the difference in deviance between the model and the null model was calculated (prediction using only the intercept term). The receiver operating curve (ROC) was created by plotting the true positive rate (TPR, sensitivity) against the false positive rate (FPR, 1—precision) at various threshold settings. The area under the ROC curve ($\text{AUC}_{ROC}$) is a measure of how well a binary classifier, based on the logistic fit, separates the two classes of events, with an $\text{AUC}_{ROC}$ of above 0.5 being better than random guessing. In addition, the area under the precision recall (PR) curve ($\text{AUC}_{PR}$) was computed, which plots precision over recall (sensitivity). Precision is the percentage of true positive detections in all positive detections and is a good measure of the classifier's performance in highly imbalanced datasets as it is not affected by the imbalanced sample proportions. Confidence intervals on AUC metrics were computed empirically with 1000 bootstrap replicas. Using the method outlined by Delong et al., we compared the $\text{AUC}_{ROC}$ for each metric against the $\vec{\theta}_{brain}$ criteria to test for statistical significance (E. R. Delong, et al. (1988) *Biometrics*, 44, 837-845, the disclosure of which is incorporated herein by reference). In all statistical analyses, multiple comparisons were accounted for using the Bonferroni correction method. In this method, the standard significance value of 0.05 is divided by the total number of comparisons, setting the cutoff value to be p<0.004.

In classifying rare events, where the rate of incidence in a certain class is disproportionally smaller than the other class or classes, the maximum likelihood estimation of the logistic model suffers from small sample bias. The degree of bias is strongly dependent on the number of cases in the less frequent of the two categories. Reported concussions in sports occur at a rate of close to 5.5 cases per 1000 head impacts, which is by definition a rare event. This needs to be taken into account when performing statistical analysis such as logistic regression. In addition, a majority of previously published injury criteria from injury and non-injury events have been based on severely skewed data sources, meaning that in such analysis, the percentage of injury-inducing head impacts is by a large much greater than the actual incidence rate. A formal approach was used to address these two challenges by applying Prior Correction and Bias Correction methods proposed by King and Zeng for logistic regression analysis, using the ReLogit package in R (G. King and L. Zengh (2001) *Polit. Anal.* 9, 137-163, the disclosure of which is incorporated herein by reference).

Results

Figure 7:
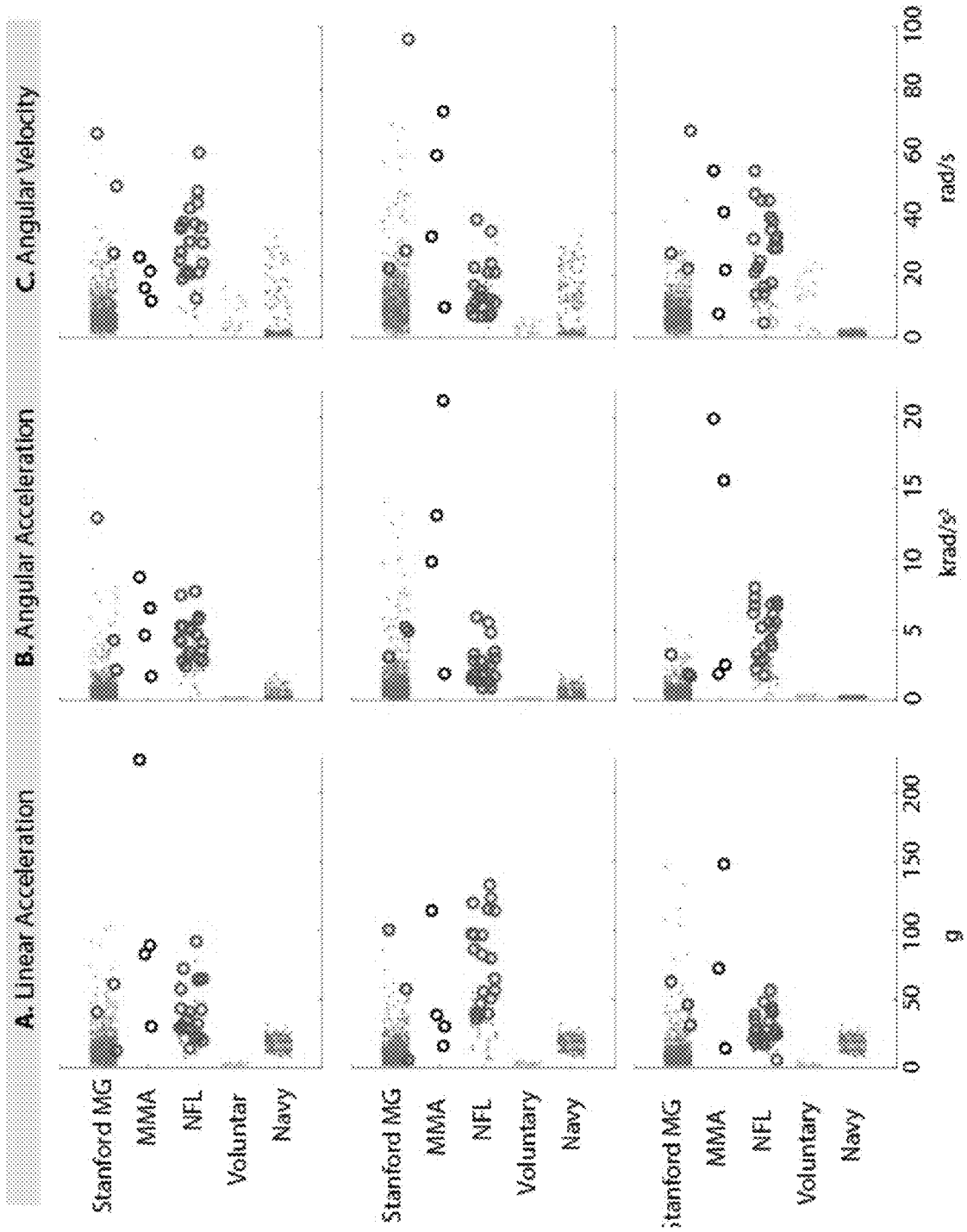
FIG. 7 provides data charts showing distribution of linear and rotational kinematics in each anatomical plane, utilized in accordance with various embodiments.
Figure 8:
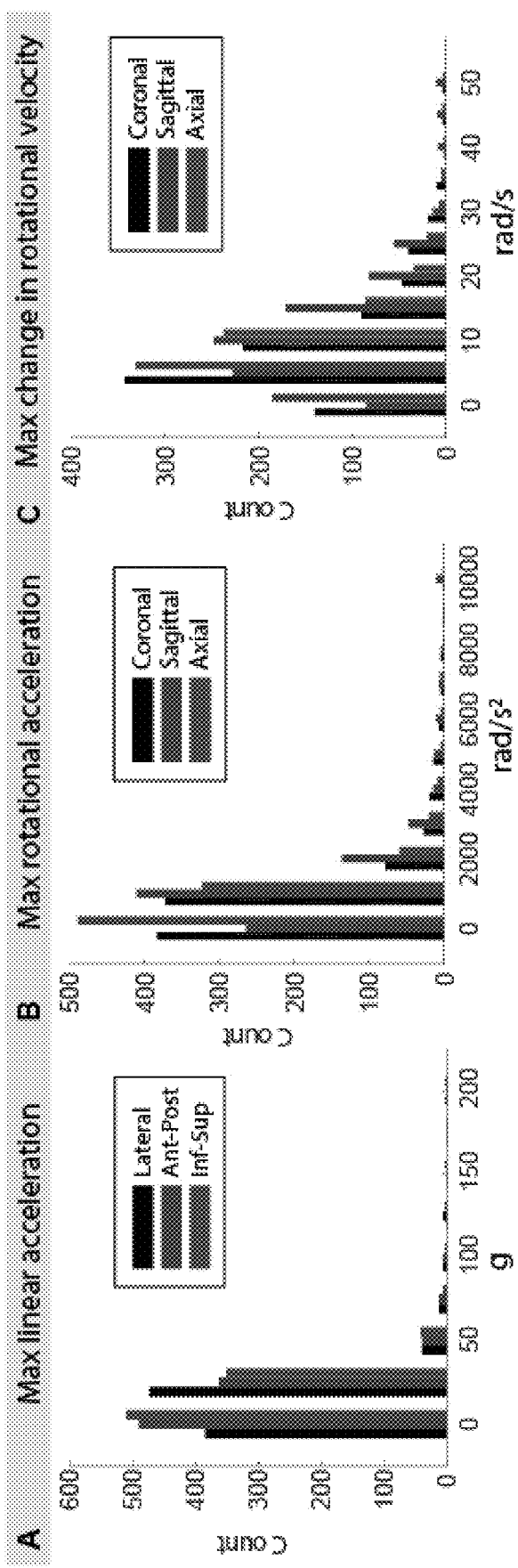
FIG. 8 provides data histogram charts showing distribution of head kinematics and comparison of directional kinematics in linear acceleration, rotational velocity, and rotational acceleration, utilized in accordance with various embodiments.

A total of 914 head kinematics including 27 clinically diagnosed brain injuries, from American football, boxing, mixed martial arts, sled tests, and rapid voluntary head motions were included. The translational and rotational accelerations as well as rotational velocities are shown in FIG. 7. The incidence of each kinematic measure is presented in the histogram plots in FIG. 8.

Figure 9:
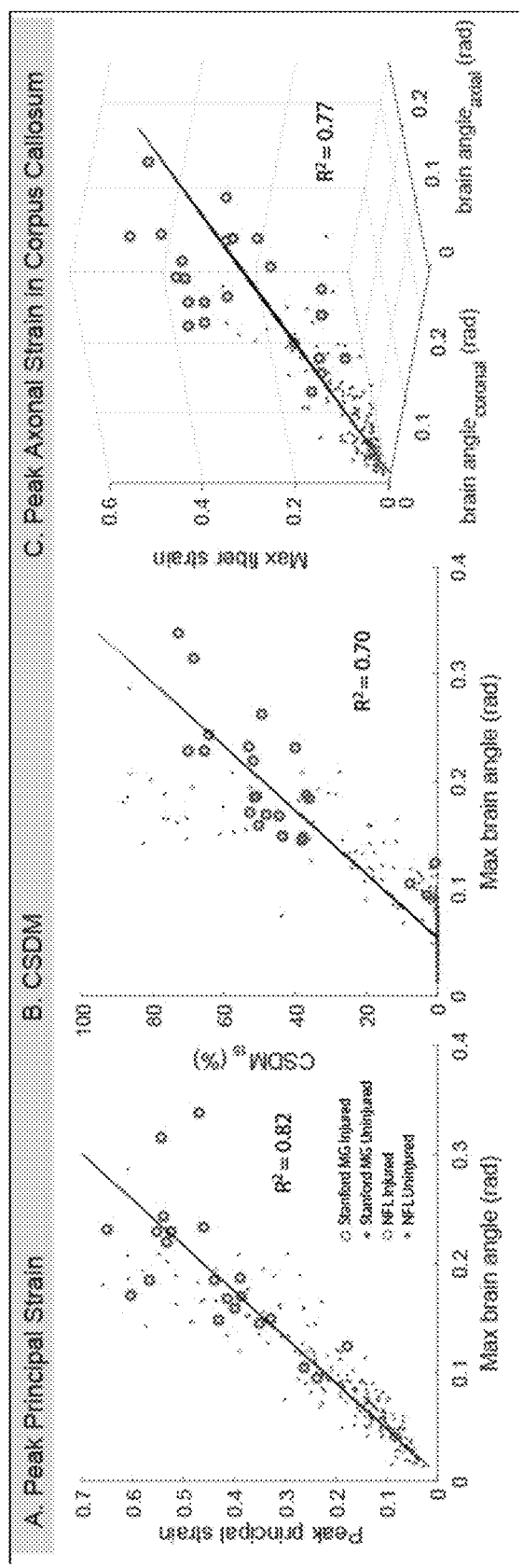
FIG. 9 provides data charts comparing the maximum relative brain displacements ($\vec{\theta}_{brain}$) predicted from the lumped model against finite element results, generated in accordance with various embodiments.

Three strain-based FE metrics were used to compare against the output of the developed lumped-parameter model, $\vec{\theta}_{brain}$: peak principal strain ($\epsilon_{max}$) and CSDM15, which are common metrics in the injury biomechanics field (FIG. 9). Strain was also used in the axonal fiber directions, a relatively new metric that has been shown to be a better predictor of microstructural damage to the brain tissue and may be appropriate for the analysis of mild TBI (FIG. 9). $\vec{\theta}_{brain}$ follows the $\epsilon_{max}$ trends closely. The linear fit begins to deviate at higher levels of strain (>30%), indicating less accurate approximations by the lumped parameter model in more severe head motions. When analyzing peak axonal strain in the corpus callosum, a three-dimensional linear regression against the peak brain displacement was first run in each plane of motion and found that the sagittal brain displacement had no significant correlation with strain in the corpus callosum. Re-running the linear regression while excluding the sagittal brain angle direction, it was found that the mechanical model was well correlated with axonal strains in the corpus callosum. For all further analyses, the results from the 3D lumped-parameter model was used due to computational cost of finite element simulation of all the events.

Figure 10:
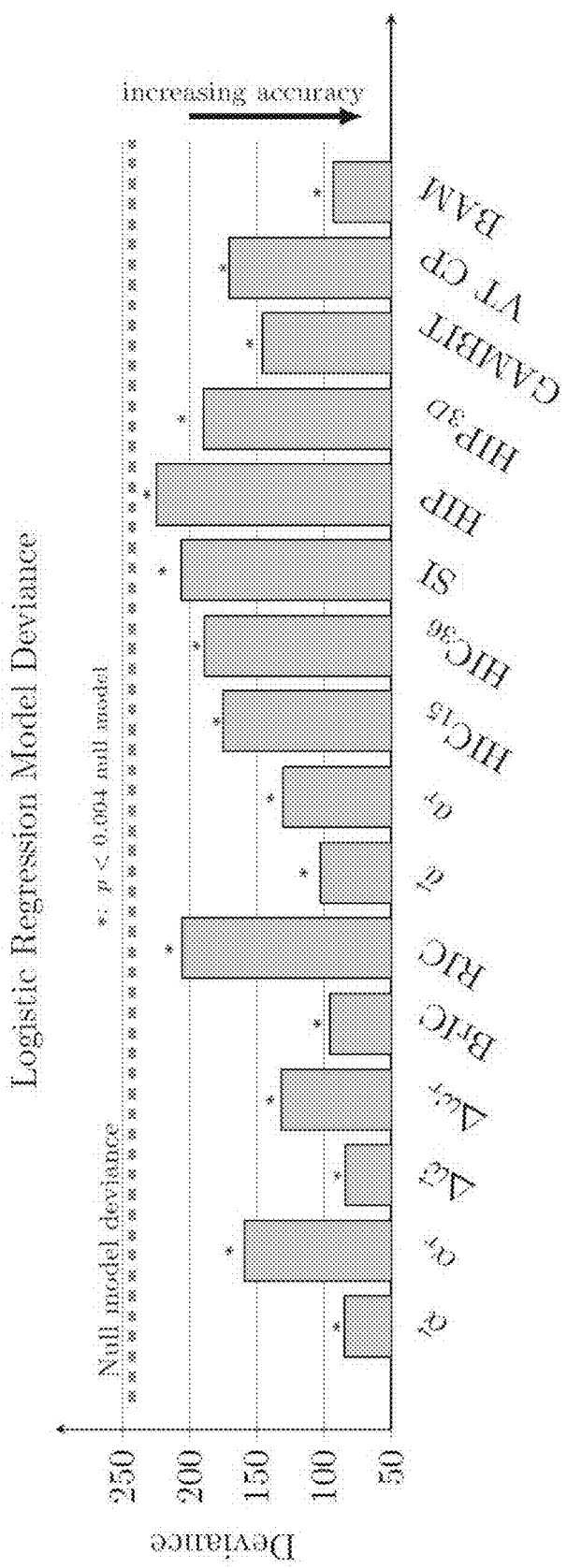
FIG. 10 provides a data graph of a statistical measure which quantifies the "goodness-of-fit" of each logistic regression, with lower values indicating a better fit, generated in accordance with various embodiments.
Figure 11:
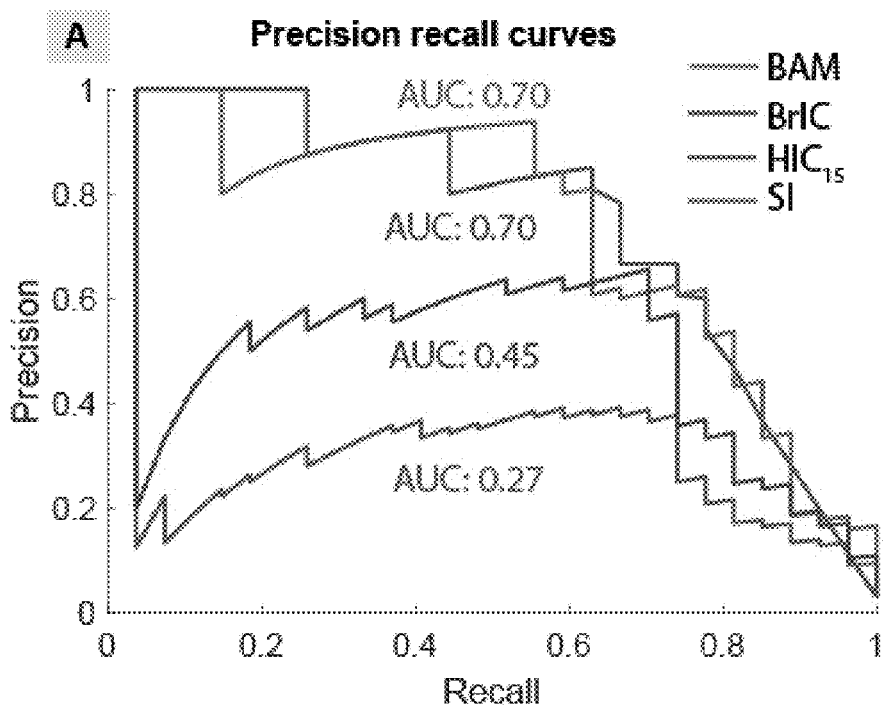
FIGS. 11 and 12 provide data graphs comparing brain angular metric (BAM) to three different commonly used metrics: BrIC, $HIC_{15}$, and SI, generated in accordance with various embodiments.
Figure 12:
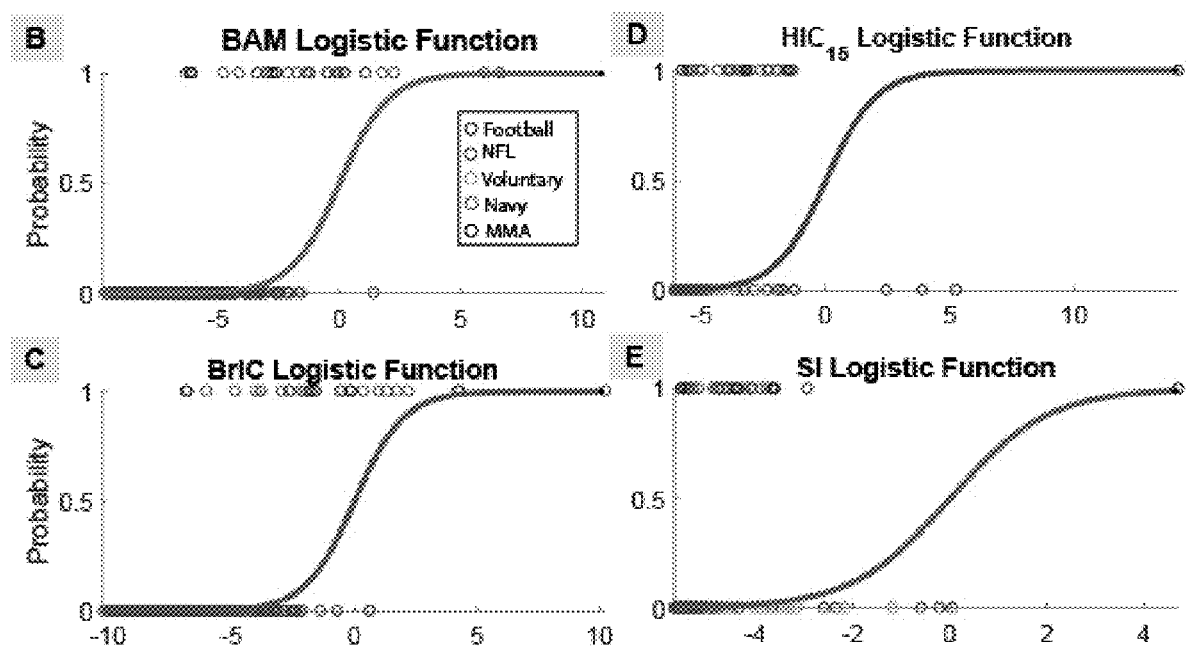
Figure 13:
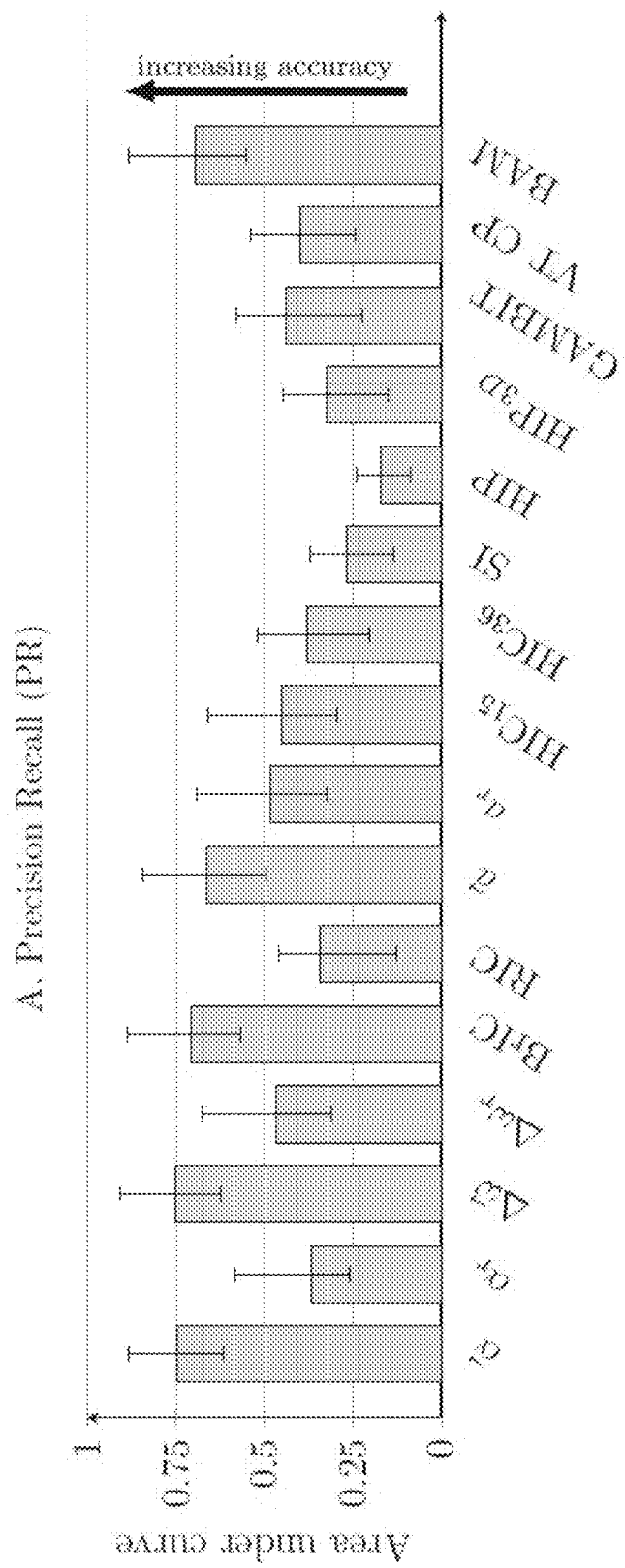
FIG. 13 provides a data graph displaying precision recall curves of various regression models, generated in accordance with various embodiments.
Figure 14:
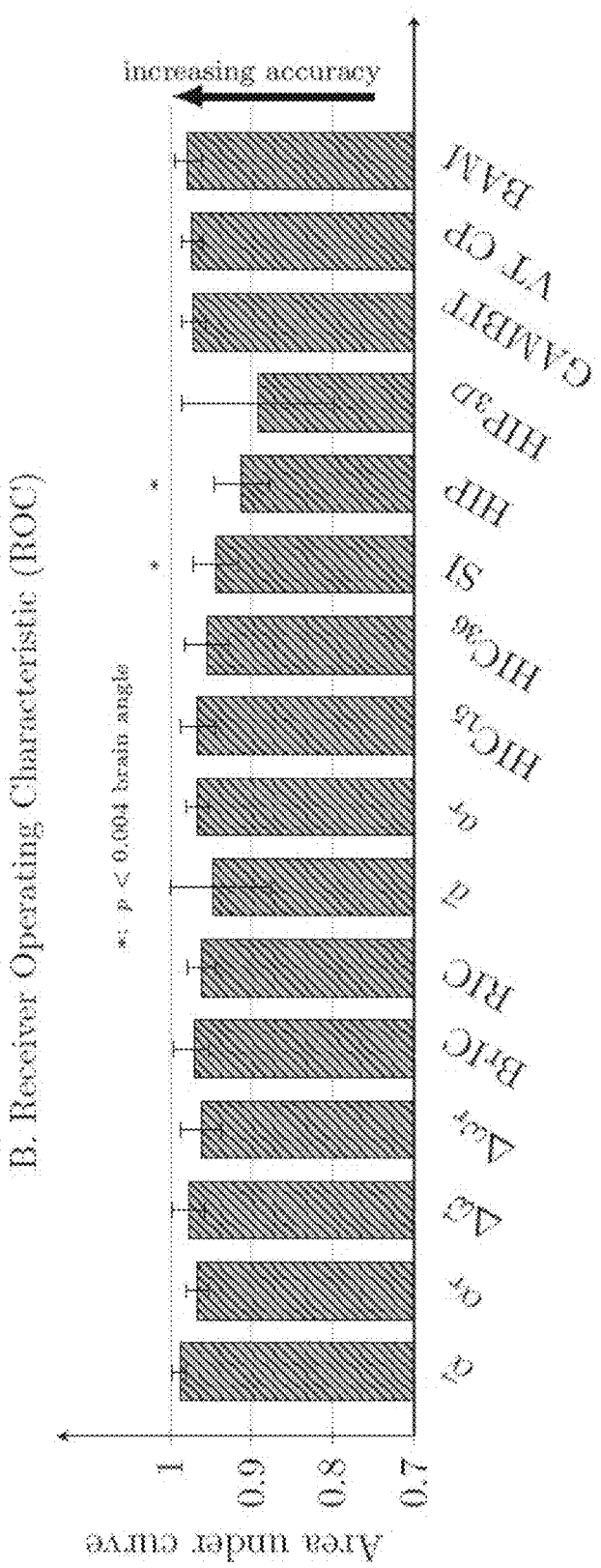
FIG. 14 provides a data graph displaying receiver operating characteristic curves of various regression models, generated in accordance with various embodiments.

Next, the performance of the kinematic injury metrics was compared with that of BAM, our metric based on the $\vec{\theta}_{brain}$ output of the lumped-parameter model, in classifying the clinical injury diagnosis of each event. It was hypothesized that since brain-skull is a dynamic system, a good predictor needs to take into account not only the peak kinematics of the head motion, but also the internal dynamics of skull and brain to account for any lag of the brain's mass. The results are shown in FIGS. 10 to 14. In FIG. 10, the deviance of each model fit is plotted, with a lower deviance indicating a better model fit. All metrics performed significantly better than the null model (a fit using a single intercept value), as denoted with asterisks. BAM had among the lowest deviance, performing comparably to $\vec{\alpha}$, $\vec{a}$, BRIC, and $\Delta\vec{\omega}$ metrics. In FIGS. 11 and 12, the precision recall curve of BAM was compared with three commonly-used kinematic metrics: BrIC, HIC, and SI. Further, the four logistic regression functions with injury and non-injuries from each data source are shown. The rotational metrics (BrIC and BAM) had much higher sensitivity, precision and $\text{AUC}_{PR}$ than metrics that rely on translational acceleration magnitude ($\text{HIC}_{15}$ and SI). The $\text{AUC}_{ROC}$ and $\text{AUC}_{PR}$ for all models are also shown in FIGS. 13 and 14. BAM was among the metrics with $\text{AUC}_{PR}$ of above 0.70, with the others being $\vec{\alpha}$, $\Delta\vec{\omega}$, and BrIC metrics. Further, BAM shows statistically significantly larger $\text{AUC}_{ROC}$ over RIC, SI, and HIP, with comparable $\text{AUC}_{ROC}$ to $\vec{\alpha}$, $\Delta\vec{\omega}$, and BrIC metrics. Vector metrics $\vec{\alpha}$, $\Delta\vec{\omega}$, and $\vec{a}$ had lower deviance and higher $\text{AUC}_{ROC}$ and $\text{AUC}_{PR}$ than the kinematic metrics based on resultant traces, $\alpha_r$, $\Delta\omega_r$, and $a_r$.

BAM's performance was compared to $\epsilon_{max}$ on the subset of the 169 simulated football head impacts. Specifically, a logistic regression models was fit to $\epsilon_{max}$, $\theta_{brain}{}^r$ (max resultant brain angle), and BAM ($\vec{\theta}_{brain}$, the maximum brain angle in each direction). On this smaller dataset, $\epsilon_{max}$ had a deviance of 98.64, $\text{AUC}_{ROC}$ of 0.91, and $\text{AUC}_{PR}$ of 0.65, while $\theta_{brain}{}^r$ had a deviance of 93.10, $\text{AUC}_{ROC}$ of 0.92, and $\text{AUC}_{PR}$ of 0.74. BAM had a deviance of 64.93, $\text{AUC}_{ROC}$ of 0.96, and $\text{AUC}_{PR}$ of 0.88.

Note that Prior Correction and Bias Correction have been applied to adjust for the sample proportion bias in consideration of real-world concussion incidence rates. It was found that these analyses made a difference in the fitted logistic parameters. For example, in the case of BAM, the beta coefficients in the logistic regression change from $\beta_{original}=[8.288, -29.59, -10.35, -39.38]$ to $\beta_{corrected}=[9.845, -28.86, -10.23, -37.94]$. Beta coefficients for all model logistic regression fits are shown in the in Table 3.

Figure 15:
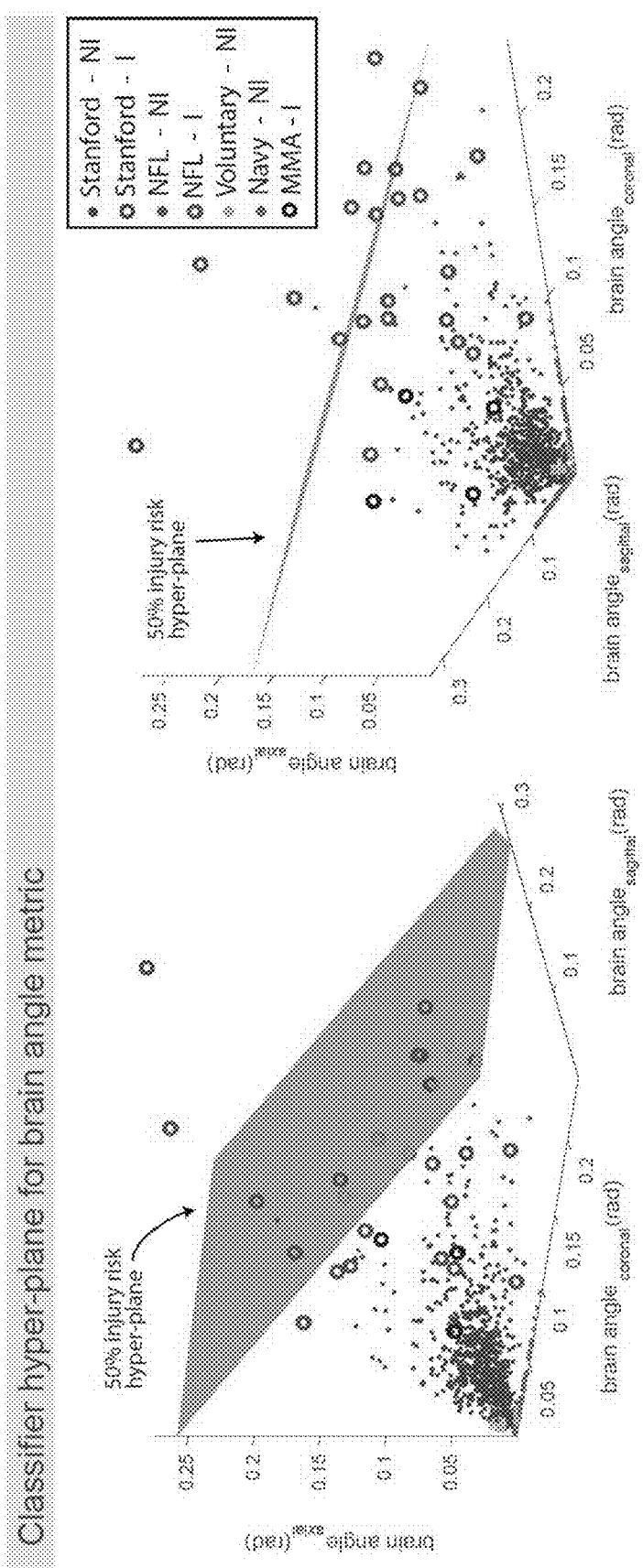
FIG. 15 provides data graphs displaying logistic regression results based on brain angle metric, generated in accordance with various embodiments.
Figure 16:
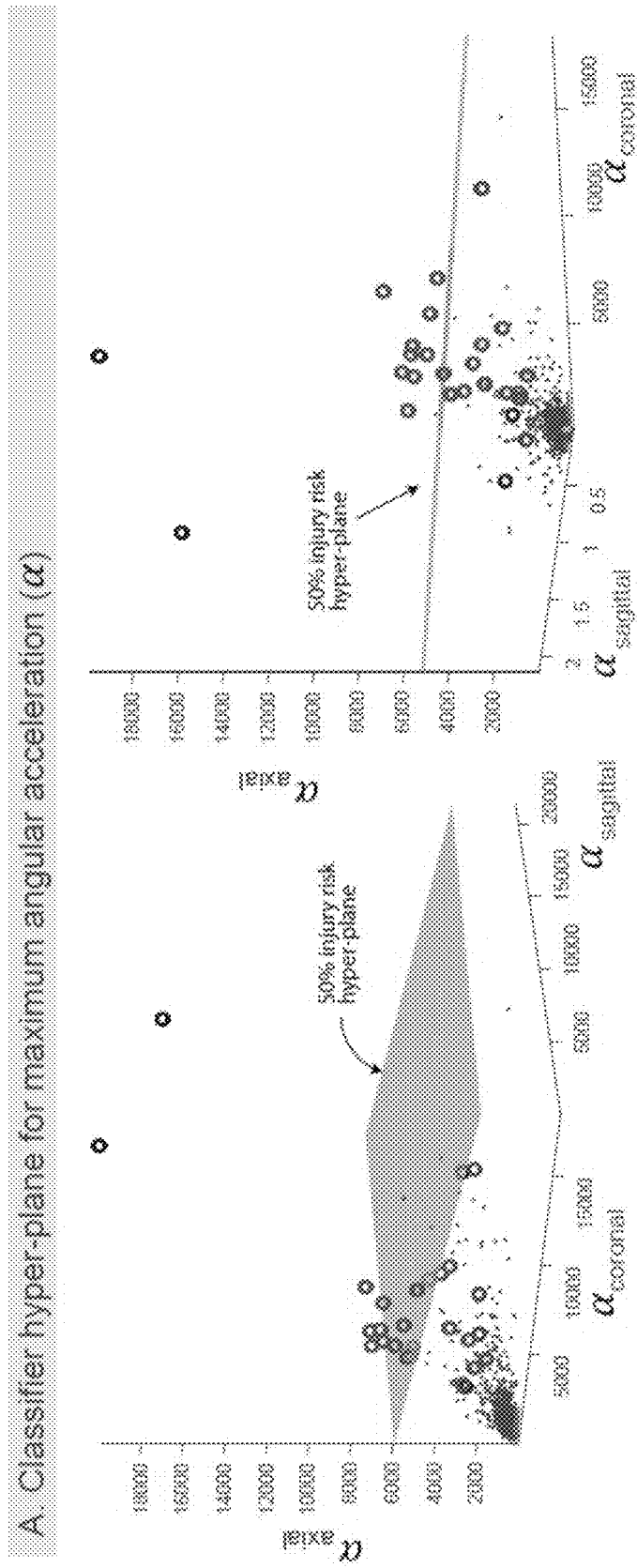
FIG. 16 provides data graphs displaying logistic regression results based on maximum angular acceleration, generated in accordance with various embodiments.
Figure 17:
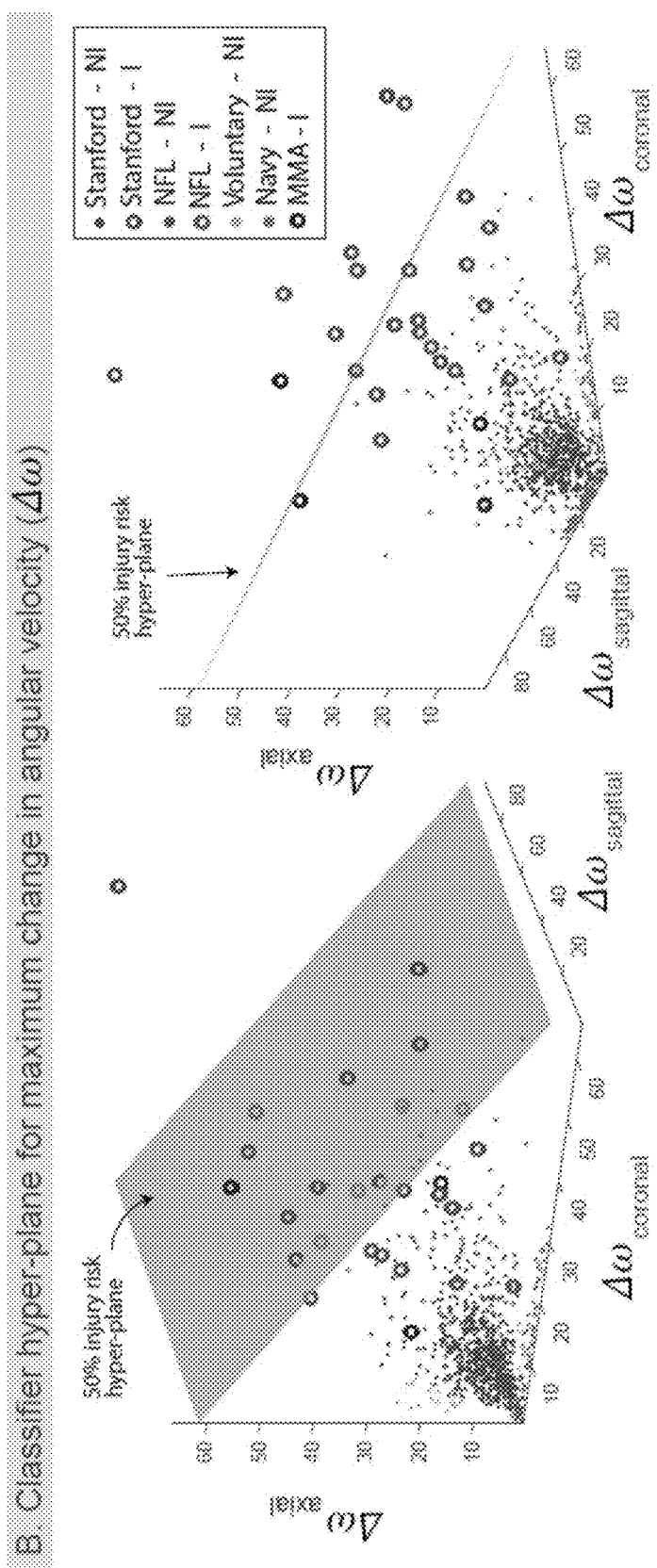
FIG. 17 provides data graphs displaying logistic regression results based on maximum change in angular velocity, generated in accordance with various embodiments.

Using BAM, a risk curve was developed to classify the injury and non-injury events. The results are given in FIG. 15, where 50% risk of concussion signified by the green plane. Critical brain angle values (axes intercept) for 50% injury risk correspond to 0.34 rad in the coronal direction, 0.26 in the axial direction, and 0.96 in the sagittal direction. In the case of classifying concussions, a high sensitivity classifier is desirable to minimize the number of false negatives. The classifier hyper-plane can be tuned to different sensitivity levels by adjusting the classification threshold. To obtain 50% sensitivity with the BAM, coronal, sagittal, and axial critical values are 0.29, 0.83, and 0.22; to obtain 90% sensitivity, the critical values are 0.17, 0.49, and 0.13. Risk curves for $\vec{a}$ and $\Delta\vec{\omega}$ are shown in FIGS. 16 and 17.

TABLE 3

Logistic regression coefficients for each tested metric.

| | $\beta_0$ | $\beta_1$ | $\beta_2$ | $\beta_3$ |
|---|---|---|---|---|
| $\vec{\alpha}$ | 8.446 | −1.63e−4 | 5.17e−5 | −.0014• |
| $\alpha$ | 6.900 | −4.74e−4• | — | — |
| $\Delta\vec{\omega}$ | 10.69 | −.145• | −.005 | −.172• |
| $\Delta\omega_r$ | 7.421 | −.122• | — | — |
| BrIC | 10.57 | −11.10• | — | — |
| RIC | 5.559 | −4.3e−8• | — | — |
| $\vec{\alpha}$ | 9.041 | −.071• | −.071• | −.031• |
| $\alpha_r$ | 8.038 | .0572 | — | — |
| $HIC_{15}$ | 6.071 | −.0072• | — | — |
| $HIC_{36}$ | 5.928 | −.0056• | — | — |
| SI | 5.673 | −.0024• | — | — |
| HIP | 5.549 | −4.11e−5• | — | — |
| HIP3D | 5.882 | −1.43e−5 | −2.26e−4• | 1.50e−4 |
| GAMBIT | 5.701 | −9.599• | — | — |
| VT CP | 5.910 | −5.126• | — | — |
| BAM | 9.845 | −28.83 | −10.23 | −37.95• |

Statistical significance (p < 0.05) denoted by asterisk.

Supplementary Materials
Injury Data Points

All injury points in our dataset involved a clinical diagnosis of concussion from a physician due to either loss of consciousness or neurological testing that indicated significant post-concussive symptomology. The two injury data points from collegiate football are described in Hernandez et al[24]. The 20 injury data points from NFL reconstructions are described by Pellman et al.[36] and Sanchez et al.[25]. Four injuries were recently measured in a professional MMA event using the Stanford Instrumented Mouthguard[29]. To assess neurological impairment, the Sport Concussion Evaluation Tool (SCAT5)[63] neurological test was performed on each fighter prior to the fight and within 120 hours after the completion of the fight. Two fighters were knocked out and loss consciousness thus ending the bout; both of these fighters were diagnosed with concussion, and the impact which caused the knockout was used for analysis in this paper. The remaining two fighters experienced a significant increase in SCAT5 symptom score post-fight with complaints of migraines and other symptoms indicative of post-concussive syndrome. Both fighters were clinically diagnosed with a concussion. For these two fighters, because it was not clear which impact caused the concussion, the impact with the highest peak angular acceleration magnitude experienced over the entire fight was used for analysis in this paper. The final injury data point was taken from a recent study funded by Taube Philanthropies to instrument high school football athletes with the Stanford Instrumented Mouthguard. Thus far, one concussion has been recorded, which was clinically diagnosed by a physician at the end of the game through symptom evaluation. The recorded impact with the highest angular acceleration value near the time of the concussive event was used for analysis in this study. The data from Ewing et al[26,27,40] was measured in 1975-1978, where the definition of "concussion" could be quite different from the modern definition. However, all subjects in these studies underwent clinical evaluation before and after each run, and none suffered from an alteration of consciousness or detectable neurological deficit attributable to the head acceleration exposure, thus justifying their inclusion as non-injury impacts.

Injury Criteria

The following rotational kinematics-based injury criteria were computed to compare against the rigid body brain displacement model:

Peak Angular Acceleration ($\vec{\alpha}$) was a vector defined as the maximum value of the rotational acceleration time series in each anatomical direction, $$\vec{\alpha}=[\max|\alpha_x| \max |\alpha_y| \max|\alpha_z|]$$

The maximum was taken over the entire recorded time for a given time series.

Peak Change in Rotational Velocity ($\Delta\vec{\omega}$) was defined as the largest change in rotational velocity magnitude in each anatomical direction, $$\Delta\vec{\omega}=|\max \omega_x(t)-\min \omega_x(t) \max \omega_y(t)-\min \omega_y(t) \max \omega_z(t)-\min \omega_z(t)|$$

The maximum and minimum for each component are taken over the entire recorded time series.

Brain Injury Criterion (BrIC)[18] was developed by National Highway Traffic Safety Administration (NHTSA) to account for diffuse axonal injury. It is based on Cumulative Strain Damage Measure (CSDM) values and uses critical values derived from finite element simulations:

$$BrIC = \sqrt{\left(\frac{\omega_x}{\omega_{xC}}\right)^2 + \left(\frac{\omega_y}{\omega_{yC}}\right)^2 + \left(\frac{\omega_z}{\omega_{zC}}\right)^2}$$

$\omega_x$, $\omega_y$, $\omega_z$ are the peak values for rotational velocity in each anatomical direction over time, and $\omega_{xC}$, $\omega_{yC}$, $\omega_{zC}=[66.2, 59.1, 44.2]$ rad/s are critical values determined experimentally from frontal dummy impacts.

Peak Translational Acceleration ($\vec{a}$) was defined as the peak absolute value of the translational acceleration vector time series in each anatomical direction, $$\vec{a}=[a_x,a_y,a_z]=|\vec{a}(t)|$$

$\vec{a}$ represents the translational acceleration vector. The maximum was taken over the entire recorded time for a given time series.

Head Injury Criterion ($HIC_{15}$ and $HIC_{36}$)[10] was developed by NHTSA and is a federally-mandated injury metric in automobile safety regulation, $$HIC = \max_{t_1, t_2} \left\{ \left[ \frac{1}{t_1 - t_2} \int_{t_1}^{t_2} \|\vec{a}(t)\| dt \right]^{2.5} (t_2 - t_1) \right\}$$

$\|\vec{a}(t)\|$ is the translational acceleration magnitude, with times $t_1$ and $t_2$ chosen to maximize the value of HIC over the entire time series. $HIC_{15}$ uses $t_2-t_1<15$ ms, and $HIC_{36}$ uses bounds $t_2-t_1<36$ ms.

Rotational Injury Criterion (RIC)[64] was developed to be the angular acceleration equivalent of HIC, and is defined as, $$RIC = \max_{t_1, t_2} \left\{ \left[ \frac{1}{t_1 - t_2} \int_{t_1}^{t_2} \|\vec{\alpha}(t)\| dt \right]^{2.5} (t_2 - t_1) \right\}$$

$\|\vec{\alpha}(t)\|$ is the rotational acceleration magnitude. Times $t_1$ and $t_2$ chosen to maximize the value of HIC over the entire time series with $t_2-t_1<36$ ms.

Severity Index (SI)[9], also known as the Gadd Severity Index (GSI), is given by, $$SI = \int \|\vec{a}(t)\|^{2.5}$$

Head Impact Power (HIP)[19] includes 6 DOF measurements of angular and translational acceleration measurements of the head at the head center of gravity, as shown below, $$HIP = \max(ma_x(t)\int a_x(t)dt + ma_y(t)\int a_y(t)dt + ma_z(t)\int a_z(t)dt + I_{xx}\alpha_x(t)\int \alpha_x(t)dt + I_{yy}\alpha_y(t)\int \alpha_y(t)dt + I_{zz}\alpha_z(t)\int \alpha_z(t)dt)$$

x, y, z respectively correspond to the anterior, left, superior for translational acceleration, and to coronal, sagittal, and axial for rotational acceleration. The maximum was taken over the entire recorded time for a given time series.

Head Impact Power $(HIP_{3D})$[19] separates the components of HIP by their anatomical direction resulting in a vector with values for each anatomical plane:

$$HIP_{3D} = [HIP_x, HIP_y, HIP_z]$$

$$HIP_x = \max(ma_x(t)\int a_x(t)dt + I_{xx}\alpha_x(t)\int \alpha_x(t)dt)$$

$$HIP_y = \max(ma_y(t)\int a_y(t)dt + I_{yy}\alpha_y(t)\int \alpha_y(t)dt)$$

$$HIP_z = \max(ma_z(t)\int a_z(t)dt + I_{zz}\alpha_z(t)\int \alpha_z(t)dt)$$

x, y, z respectively correspond to the anterior, left, superior for translational acceleration, and to coronal, sagittal, and axial for rotational acceleration. The maximum was taken over the entire recorded time for a given time series.

Generalized Acceleration Model for Brain Injury (GAMBIT)[20] combines both rotational and translational components of head acceleration, calculated as, $$GAMBIT = \max\left\{ \left[ \left(\frac{\|\vec{\alpha}(t)\|}{\alpha_c}\right)^m + \left(\frac{\|\vec{a}(t)\|}{a_c}\right)^n \right]^{\frac{1}{s}} \right\}$$

Where $n=m=2$, $a_c=250$ g, $\alpha_c=25000$ rad/s$^2$. The maximum is taken over the entire recorded time series of the signal.

Virginia Tech Combined Probability Metric (VTCP) developed an injury metric which computes overall risk of brain injury based on peak translational and rotational accelerations, $$VTCP = \frac{1}{1 + e^{\beta_0 + \beta_1 a + \beta_2 \alpha + \beta_3 a\alpha}}$$

$\beta_0=-10.2$, $\beta_1=-0.0433$, $\beta_2=0.000873$, and $\beta_3=-0.000000920$. $\alpha$ is the peak rotational acceleration magnitude and a is the peak translational acceleration magnitude experienced over the entire impact.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A system for assessment of head kinematics and real-time detection of concussive events, comprising:
   a head-mounted device configured to being worn on or secured to a head of an individual, wherein the head-mounted device comprises one or more accelerometers for measuring angular head motion when worn or secured to the head of the individual; and
   a computer system in communication with the head-mounted device via an interface, wherein the computer system comprises a memory and a processor that reads instructions stored in the memory, wherein the instructions direct the processor to:
   capture in real time, utilizing the one or more accelerometers, brain angle measurements in one or more anatomical directions;
   compute in real time, utilizing the captured brain angle measurements as input in a mathematical mass-spring-damper model, a brain angle metric for the one or more anatomical directions; and
   determine in real time, utilizing the brain angle metric as input within a trained classifier, that a concussive event occurs, wherein the trained classifier is trained to classify whether the computed brain angle metric is indicative of a concussive event or a non-concussive event.

2. The system of claim 1, wherein the brain angle metric is a maximum brain angle.

3. The system of claim 1, wherein the brain angle metric is a vector of three peak brain angle values for three anatomical directions.

4. The system of claim 1, wherein the mathematical mass-spring-damper model models a rotational deformation of a brain from skull loading.

5. The system of claim 1, wherein the mathematical mass-spring-damper model computes motion for each anatomical direction utilizing:

$$I(\ddot{\theta}_{brain} + \ddot{\theta}_{skull}) = -k\theta_{brain} - c\dot{\theta}_{brain}$$

wherein I is a moment of inertia of a mass, k and c are a stiffness and damping values of the system, respectively, and $\theta_{brain}$ and $\theta_{skull}$ represent angles of a brain and a skull, respectively.

6. The system of claim 1, wherein the classifier is a regression model.

7. The system of claim 6, wherein the regression model is:

$$p_{injury}=(1+e^{-\beta_0-\Sigma\beta_i x_i})^{-1}$$

where $p_{injury}$ is a probability of concussive event, $x_i$ are components of an injury criterion, and $\beta_i$ are fitted coefficients, with i=1, ..., n, representing each of the at least one anatomical directions and n representing a number of anatomical directions.

8. The system of claim 1, wherein the concussive event is determined by a risk curve that determines a percent likelihood that a head impact was the concussive event.

9. The system of claim 1, wherein the one or more accelerometers comprises a rotational accelerometer or an array of linear accelerometers.

10. The system of claim 1, wherein the head-mounted device is: a helmet, a mouthguard, a hat, an ear protection, an eye-wear, a skin-mounted sensor, or a head band.

11. A real-time method for assessment of head kinematics and detection of concussive events, comprising:
fitting a head-mounted device on a head of an individual, wherein the head-mounted device comprises one or more accelerometers for measuring angular head motion;
capturing in real time, utilizing the one or more accelerometers, brain angle measurements in one or more anatomical directions;
computing in real time, utilizing the captured brain angle measurements as input in a mathematical mass-spring-damper model and a computer system, a brain angle metric for the one or more anatomical directions; and
determining in real time, utilizing the brain angle metric as input within a trained classifier and the computer system, that a concussive event occurs, wherein the trained classifier is trained to classify whether the brain angle metric is a concussive event or a non-concussive event.

12. The method of claim 11, wherein the brain angle metric is a maximum brain angle.

13. The method of claim 11, wherein the brain angle metric is a vector of three peak brain angle values for three anatomical directions.

14. The method of claim 11, wherein the mathematical mass-spring-damper model models a rotational deformation of a brain from skull loading.

15. The method of claim 11, wherein the mathematical mass-spring-damper model computes motion for each anatomical direction utilizing:

$$I(\ddot{\theta}_{brain}+\ddot{\theta}_{skull})=-k\theta_{brain}-c\dot{\theta}_{brain}$$

wherein I is a moment of inertia of a mass, k and c are a stiffness and damping values of the system, respectively, and $\theta_{brain}$ and $\theta_{skull}$ represent angles of a brain and a skull, respectively.

16. The method of claim 11, wherein the classifier is a regression model.

17. The method of claim 16, wherein the regression model is:

$$p_{injury}=(1+e^{-\beta_0-\Sigma\beta_i x_i})^{-1}$$

where $p_{injury}$ is a probability of the concussive event, $x_i$ are components of an injury criterion, and $\beta_i$ are fitted coefficients, with i=1, ..., n, representing each of the at least one anatomical directions and n representing a number of anatomical directions.

18. The method of claim 11, wherein the concussive event is determined by a risk curve that determines a percent likelihood that a head impact was the concussive event.

19. The method of claim 11, wherein the one or more accelerometers comprises a rotational accelerometer or an array of linear accelerometers.

20. The method of claim 11, wherein the head-mounted device is: a helmet, a mouthguard, a hat, an ear protection, an eye-wear, a skin-mounted sensor, or a head band.

* * * * *